United States Patent
Cadeddu et al.

(10) Patent No.: US 9,044,256 B2
(45) Date of Patent: Jun. 2, 2015

(54) MEDICAL DEVICES, APPARATUSES, SYSTEMS, AND METHODS

(75) Inventors: Jeffrey A. Cadeddu, Dallas, TX (US); Daniel J. Scott, Dallas, TX (US); Raul Fernandez, Arlington, TX (US); Richard A. Bergs, Grand Prairie, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 1039 days.

(21) Appl. No.: 12/783,440

(22) Filed: May 19, 2010

(65) Prior Publication Data

US 2011/0283822 A1    Nov. 24, 2011

(51) Int. Cl.
*A61B 17/00*    (2006.01)
*A61B 19/00*    (2006.01)
*A61B 17/29*    (2006.01)

(52) U.S. Cl.
CPC ....... *A61B 19/22* (2013.01); *A61B 2017/00278* (2013.01); *A61B 2017/00283* (2013.01); *A61B 2017/00477* (2013.01); *A61B 2017/00539* (2013.01); *A61B 2017/00876* (2013.01); *A61B 2017/2923* (2013.01); *A61B 2019/2215* (2013.01); *A61B 2019/2253* (2013.01)

(58) Field of Classification Search
CPC ....... A61B 5/06; A61B 19/2203; A61B 19/22
USPC .......... 606/1; 128/899; 600/102, 106
See application file for complete search history.

(56) References Cited

U.S. PATENT DOCUMENTS

| 6,656,194 | B1 | 12/2003 | Gannoe et al. | 606/153 |
| 7,429,259 | B2 | 9/2008 | Cadeddu et al. | 606/1 |
| 7,691,103 | B2 | 4/2010 | Fernandez et al. | 606/41 |
| 2002/0177874 | A1* | 11/2002 | Nicholas et al. | 606/206 |
| 2003/0114731 | A1 | 6/2003 | Cadeddu et al. | 600/114 |
| 2007/0135686 | A1 | 6/2007 | Pruitt et al. | 600/214 |
| 2007/0255109 | A1 | 11/2007 | Stein et al. | 600/214 |
| 2008/0167522 | A1 | 7/2008 | Giordano et al. | 600/104 |
| 2008/0269779 | A1 | 10/2008 | Cadeddu et al. | 606/130 |
| 2008/0312500 | A1 | 12/2008 | Asada et al. | 600/109 |
| 2009/0005636 | A1 | 1/2009 | Pang et al. | 600/102 |
| 2010/0030028 | A1 | 2/2010 | Cabrera et al. | 600/127 |
| 2010/0063538 | A1 | 3/2010 | Spivey et al. | 606/208 |
| 2010/0256636 | A1 | 10/2010 | Fernandez et al. | 606/49 |
| 2011/0087223 | A1 | 4/2011 | Spivey | 606/49 |

(Continued)

FOREIGN PATENT DOCUMENTS

WO    WO 2005/002415    1/2005
WO    WO 2007/130382    11/2007

(Continued)

OTHER PUBLICATIONS

U.S. Appl. No. 12/899,327, filed Oct. 3, 2010.

(Continued)

*Primary Examiner* — William Thomson
*Assistant Examiner* — Jeffrey Lipitz
(74) *Attorney, Agent, or Firm* — Norton Rose Fulbright US LLP

(57) ABSTRACT

Medical devices having a platform and an arm movable between a collapsed position and an expanded position. In some embodiments, the platform comprises at least one of a magnetically-attractive material and a material capable of being magnetically-charged. Methods of use.

9 Claims, 33 Drawing Sheets

(56) References Cited

U.S. PATENT DOCUMENTS

| | | | |
|---|---|---|---|
| 2011/0087224 A1 | 4/2011 | Cadeddu et al. | 606/49 |
| 2011/0284014 A1 | 11/2011 | Cadeddu et al. | 128/899 |
| 2011/0285488 A1 | 11/2011 | Scott et al. | 606/1 |

FOREIGN PATENT DOCUMENTS

| | | |
|---|---|---|
| WO | WO 2010/056716 | 5/2010 |
| WO | WO 2010/083480 | 7/2010 |
| WO | WO 2011/044468 | 4/2011 |
| WO | WO 2011/044471 | 4/2011 |
| WO | WO 2011/146691 | 11/2011 |
| WO | WO 2011/146709 | 11/2011 |

OTHER PUBLICATIONS

International Search Report and Written Opinion issued in PCT/US2011/037122, dated Feb. 17, 2012.

* cited by examiner

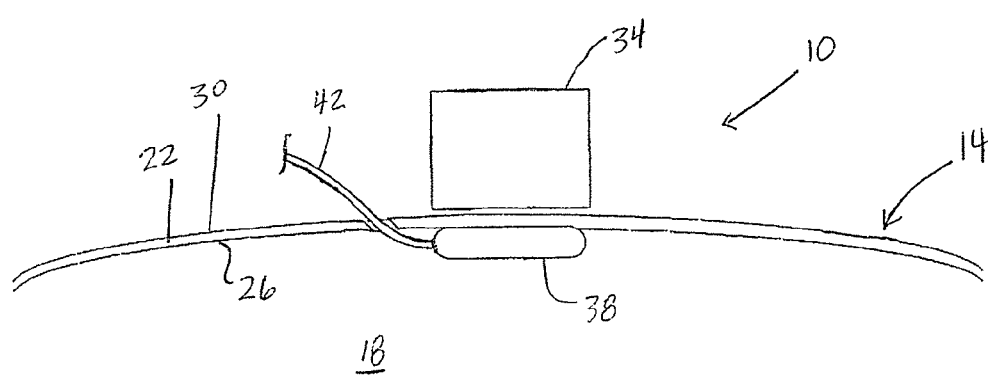
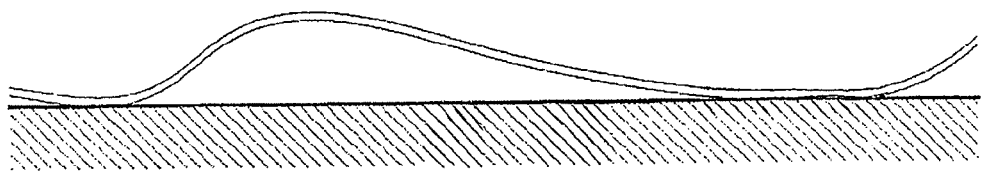
FIG. 1
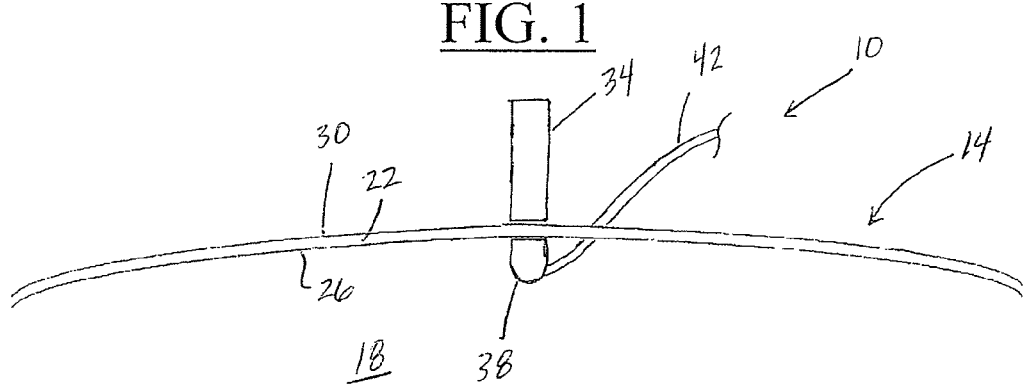
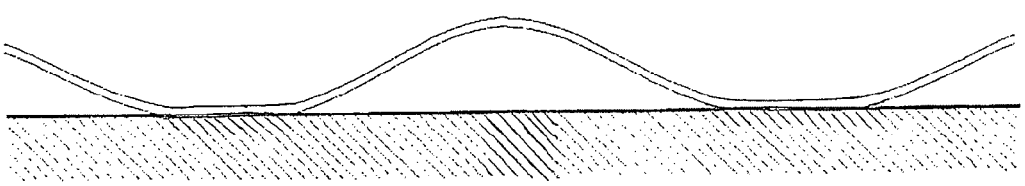
FIG. 2

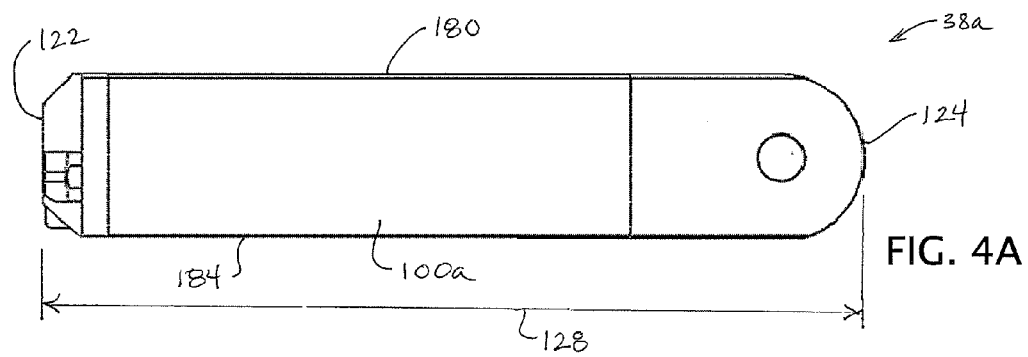
FIG. 4A
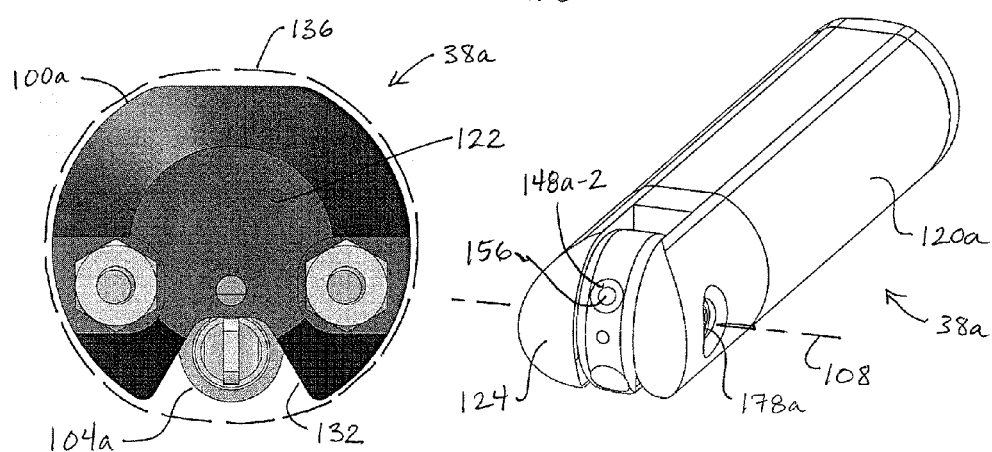
FIG. 4B
FIG. 4C
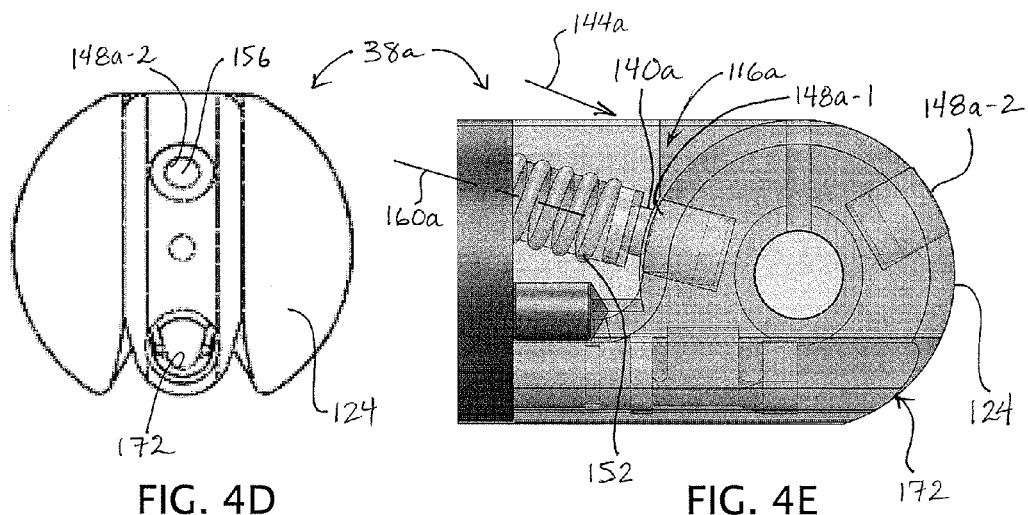
FIG. 4D
FIG. 4E

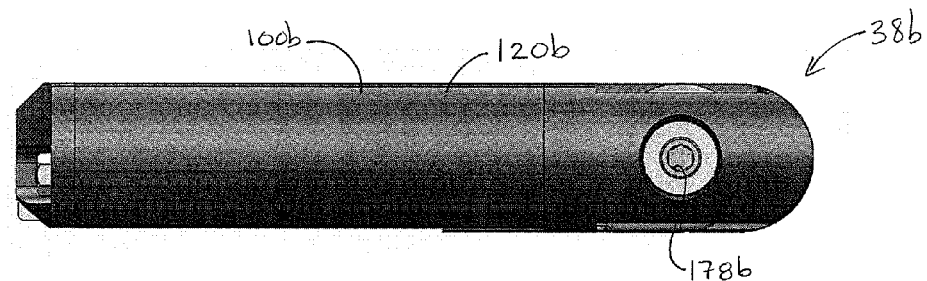
FIG. 5A
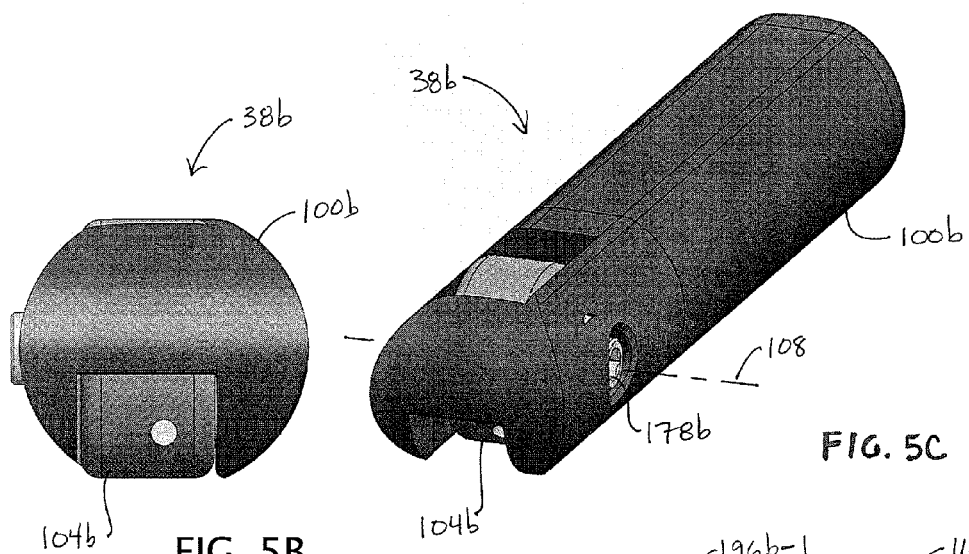
FIG. 5B
FIG. 5C
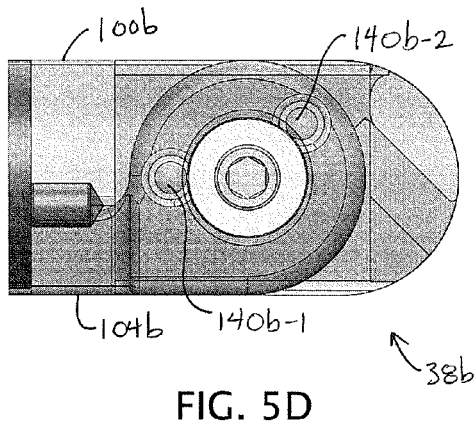
FIG. 5D
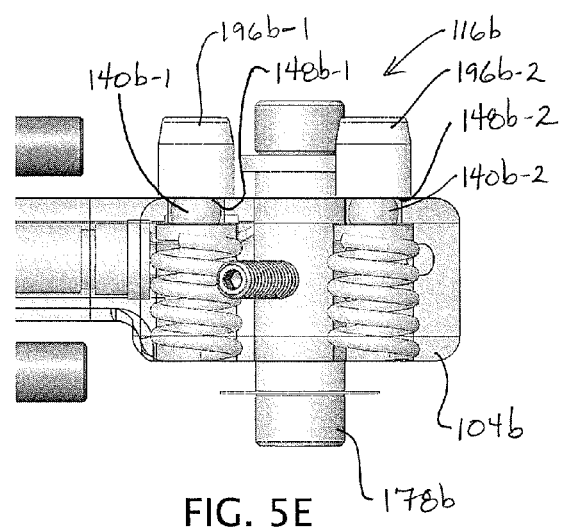
FIG. 5E

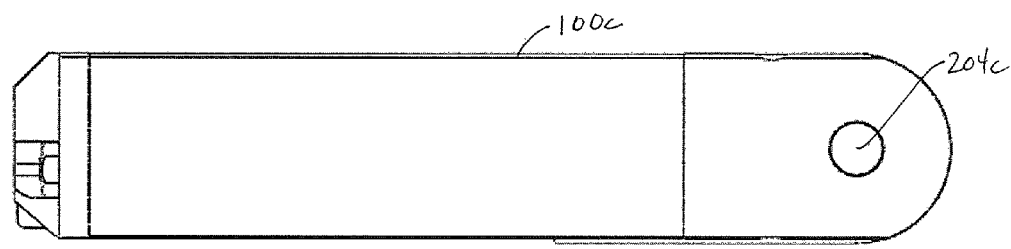
FIG. 6A
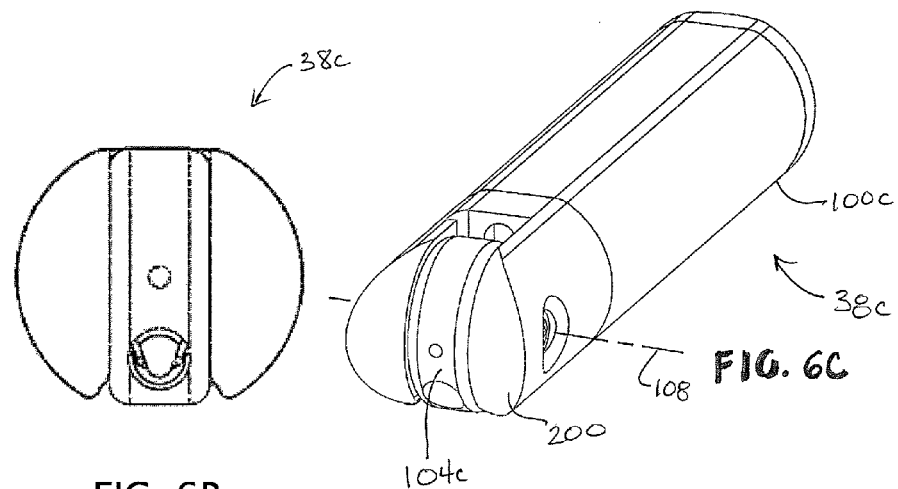
FIG. 6B
FIG. 6C
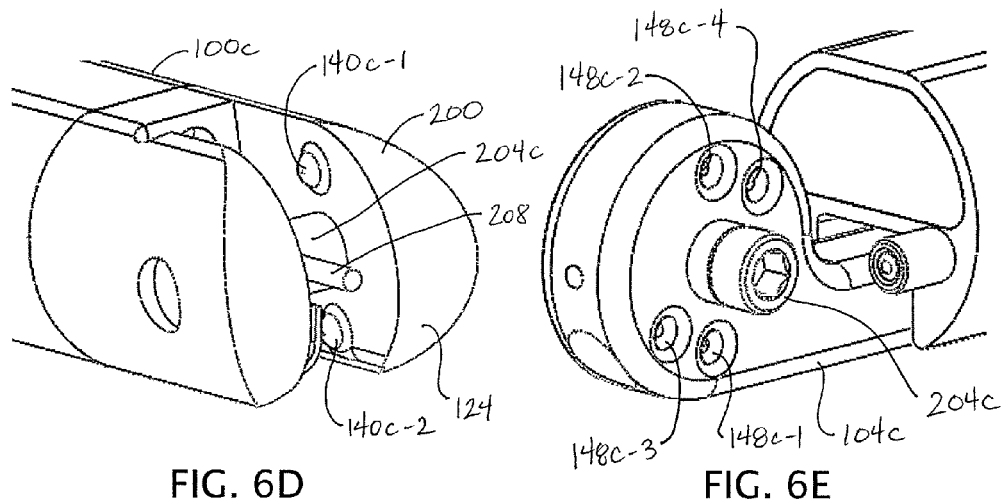
FIG. 6D
FIG. 6E

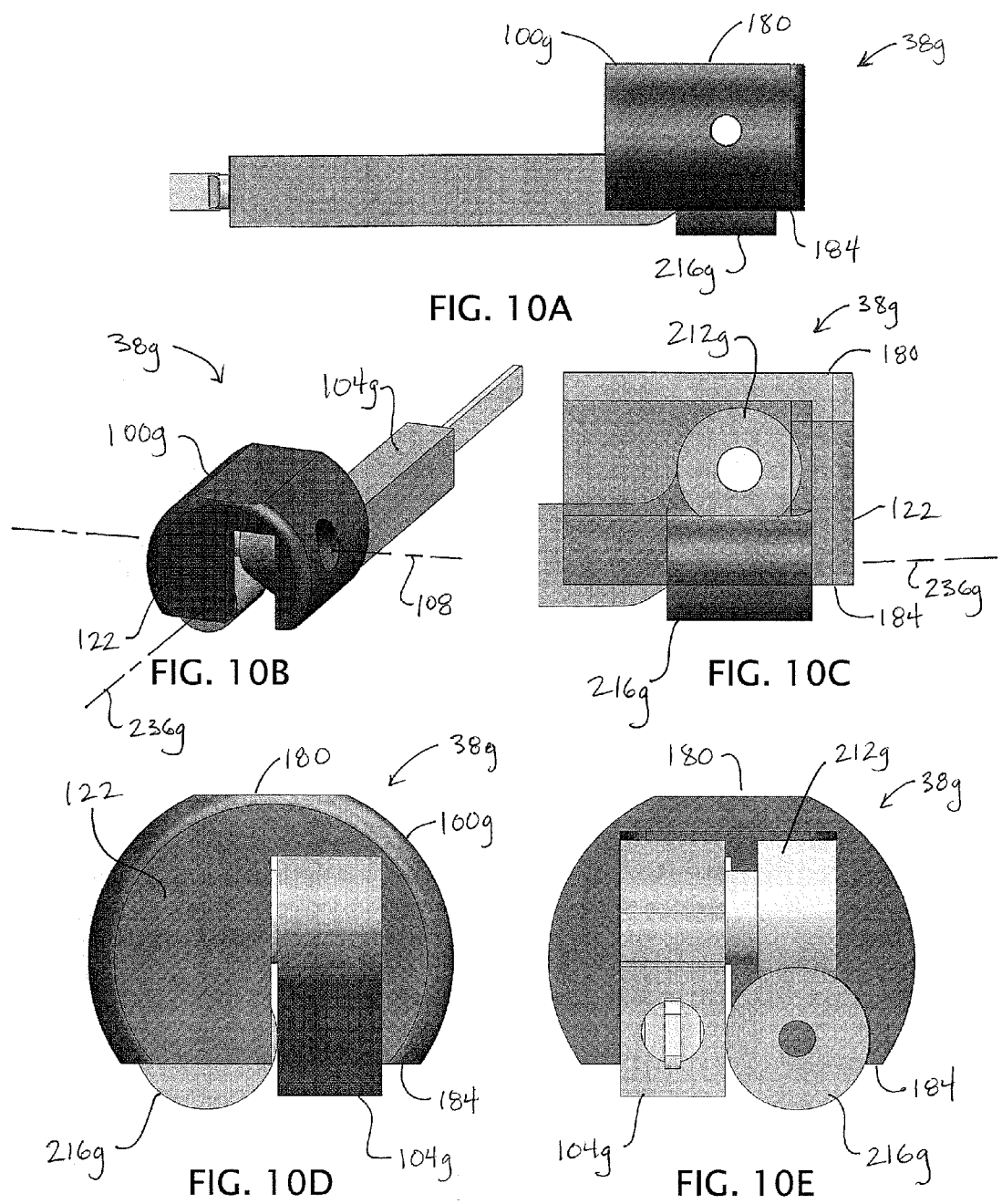

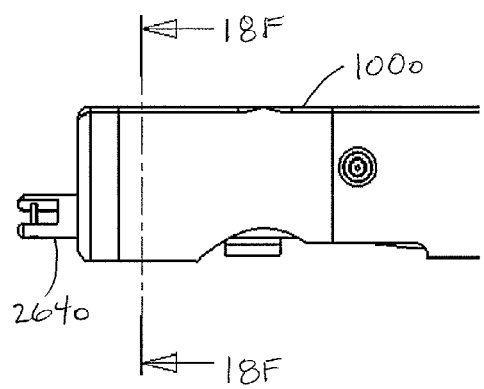
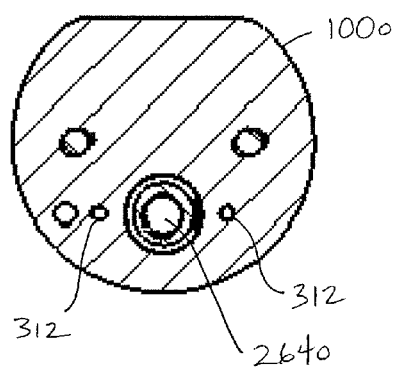
FIG. 18E  FIG. 18F
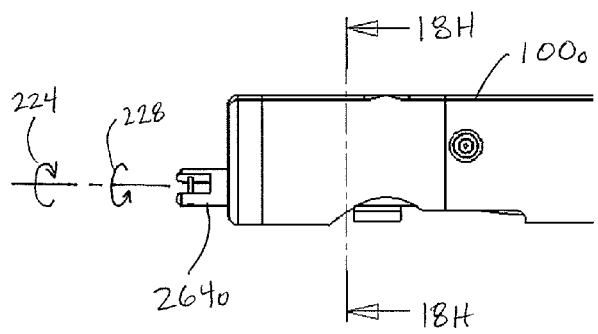
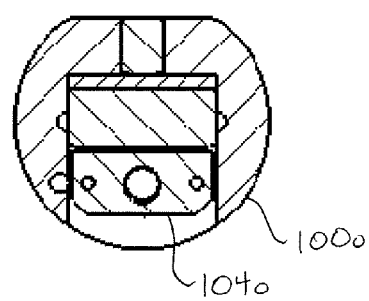
FIG. 18G  FIG. 18H

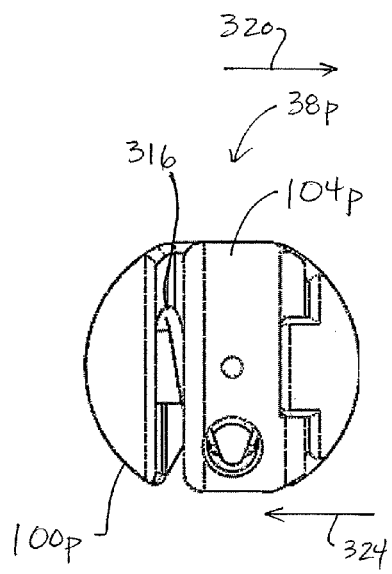
FIG. 19A
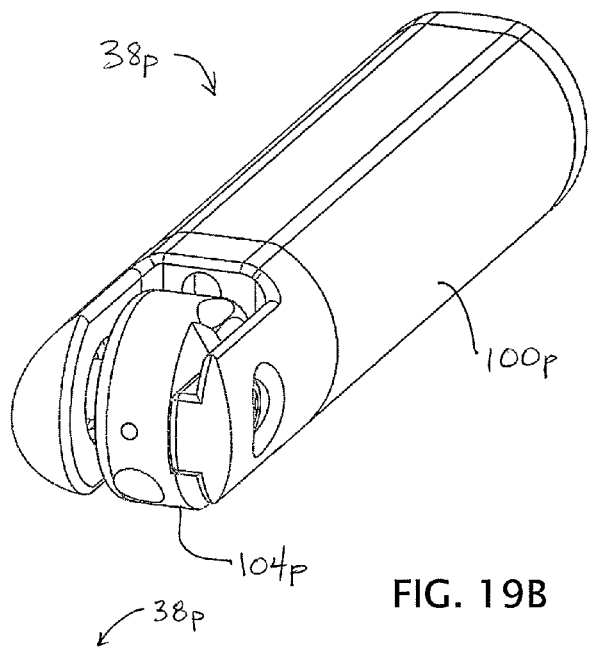
FIG. 19B
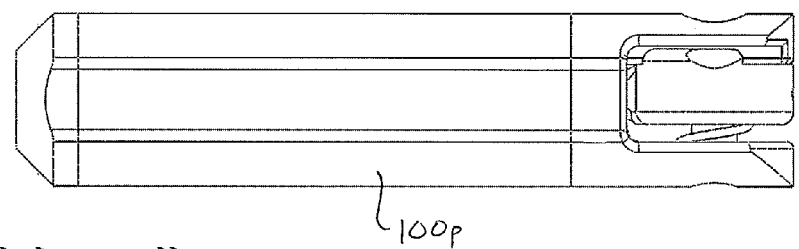
FIG. 19C
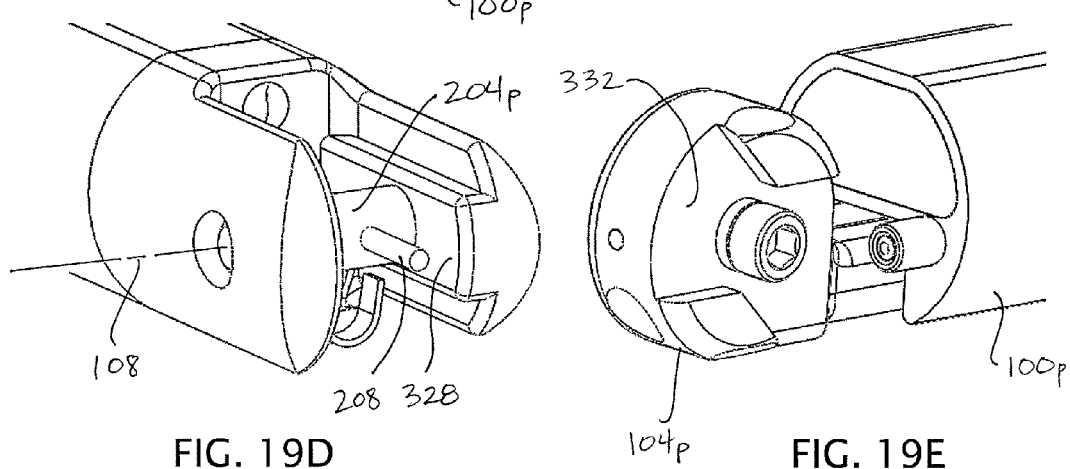
FIG. 19D
FIG. 19E

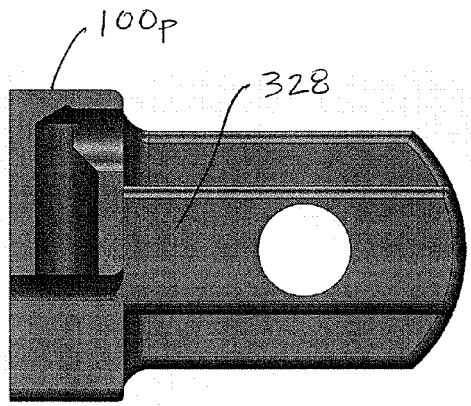
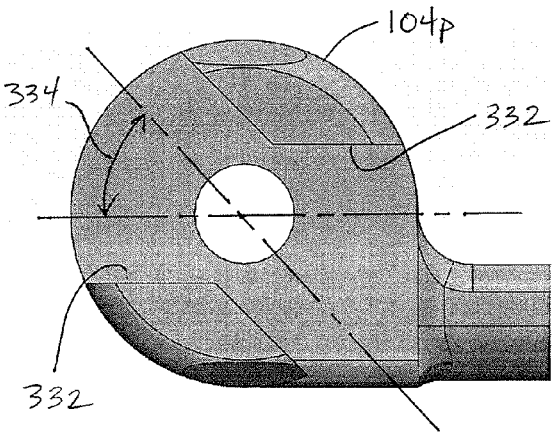
FIG. 19F          FIG. 19G
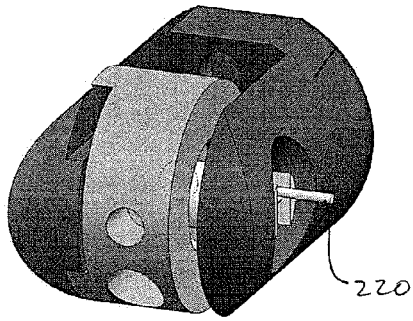
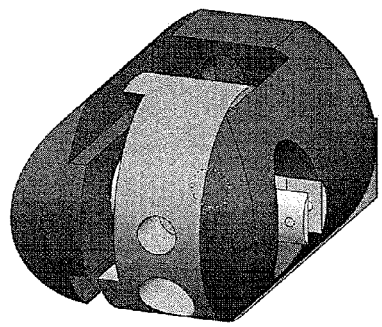
FIG. 19H          FIG. 19I
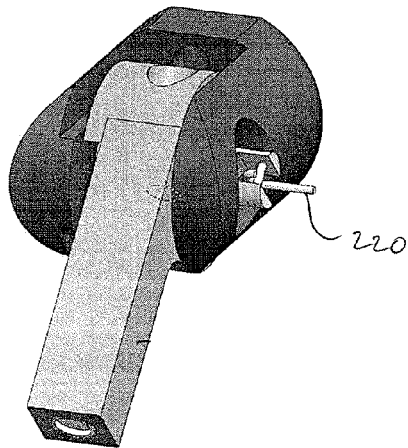
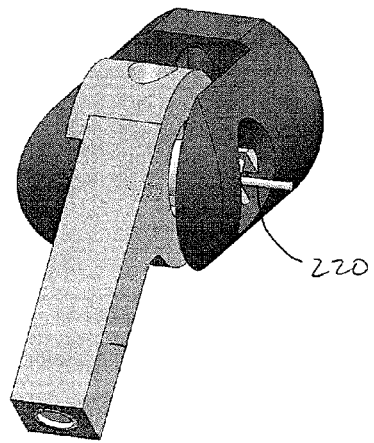
FIG. 19J          FIG. 19K

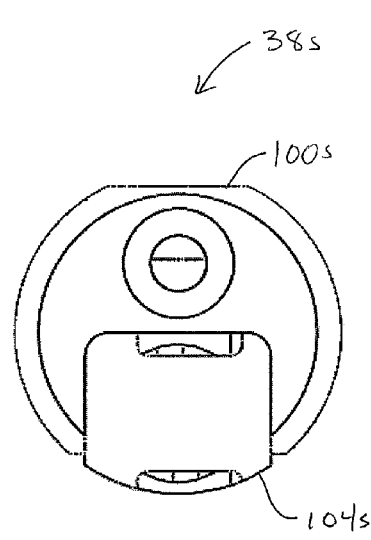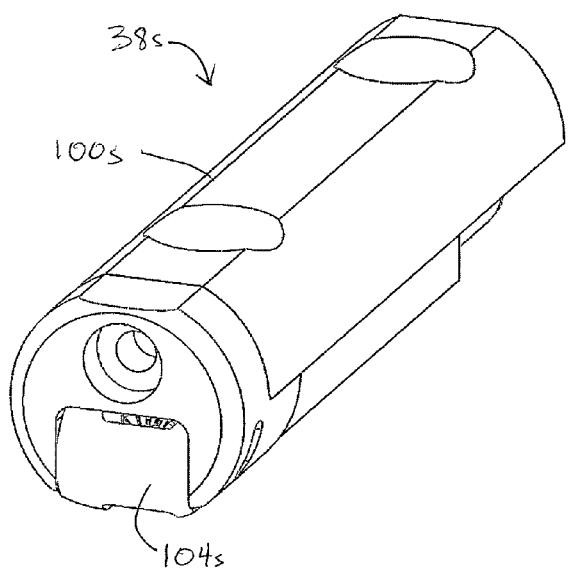
FIG. 22A  FIG. 22B
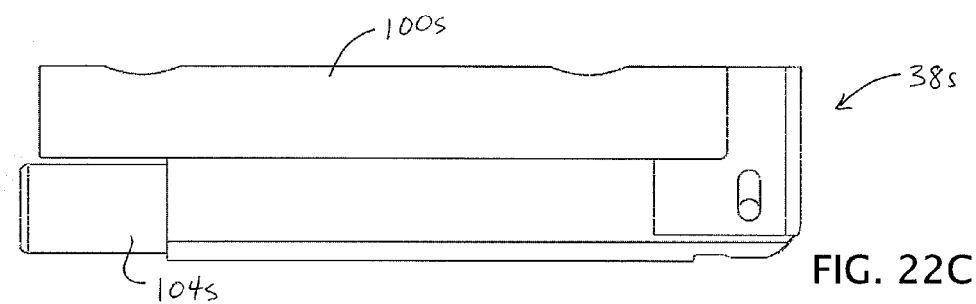
FIG. 22C
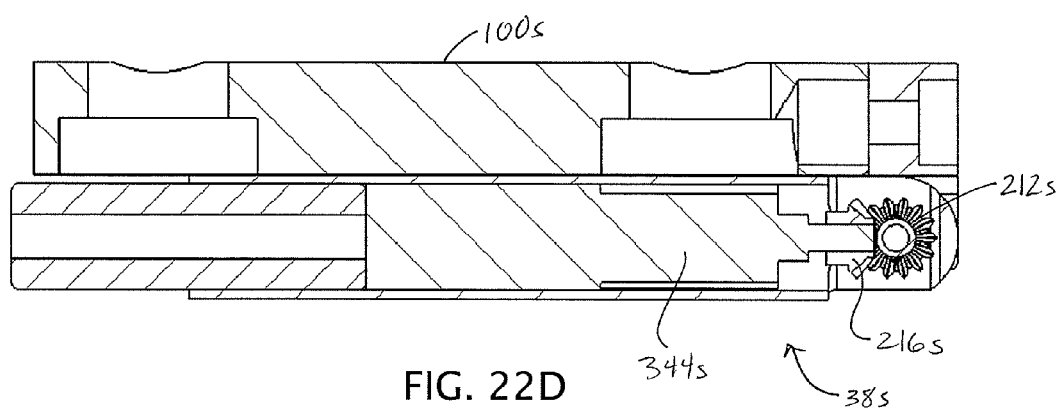
FIG. 22D

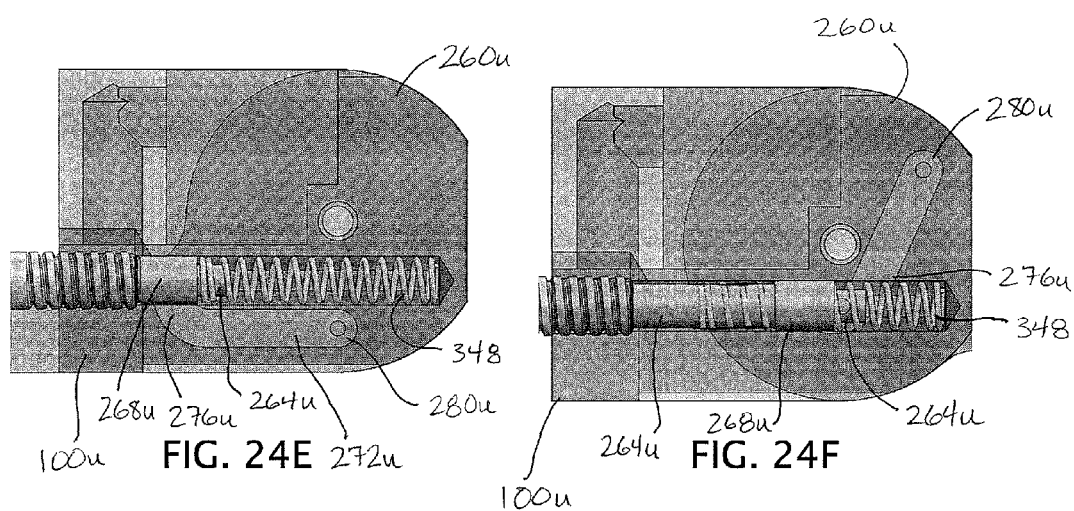

MEDICAL DEVICES, APPARATUSES, SYSTEMS, AND METHODS

BACKGROUND

1. Field of the Invention

The present invention relates generally to medical devices, apparatuses, systems, and methods, and, more particularly, but not by way of limitation, to medical devices, apparatuses, systems, and methods for performing medical procedures at least partially within a body cavity of a patient.

2. Description of Related Art

For illustration, the background is described with respect to medical procedures (e.g., surgical procedures), which can include laparoscopy, transmural surgery, and endoluminal surgery, including, for example, natural orifice transluminal endoscopic surgery (NOTES), single-incision laparoscopic surgery (SILS), and single-port laparoscopy (SLP).

Compared with open surgery, laparoscopy can result in significantly less pain, faster convalescence and less morbidity. NOTES, which can be an even less-invasive surgical approach, may achieve similar results. However, issues such as eye-hand dissociation, a two-dimensional field-of-view, instrumentation with limited degrees of freedom, and demanding dexterity requirements can pose challenges for many laparoscopic and endoscopic procedures. One limitation of laparoscopy can be the fixed working envelope surrounding each trocar. As a result, multiple ports may be used to accommodate changes in position of the instruments or laparoscope, for example, to improve visibility and efficiency. However, the placement of additional working ports may contribute to post-operative pain and increases risks, such as additional bleeding and adjacent organ damage.

The following published patent applications include information that may be useful in understanding the present medical devices, systems, and methods, and each is incorporated by reference in its entirety: (1) International Application No. PCT/US2009/063987, filed on Nov. 11, 2009; (2) U.S. patent application Ser. No. 10/024,636, filed Dec. 14, 2001, and published as Pub. No. US 2003/0114731; (3) U.S. patent application Ser. No. 10/999,396, filed Nov. 30, 2004, published as Pub. No. US 2005/0165449 and issued as U.S. Pat. No. 7,429,259; (4) U.S. patent application Ser. No. 11/741,731, filed Apr. 28, 2007, published as Pub. No. US 2007/0255273 and issued as U.S. Pat. No. 7,691,103; (5) U.S. patent application Ser. No. 12/146,953, filed Jun. 26, 2008, and published as Pub. No. US 2008/0269779; and (6) U.S. patent application Ser. No. 12/755,312, filed on Apr. 6, 2010.

SUMMARY

The present disclosure includes embodiments of medical devices, systems, and methods.

Some embodiments of the present medical devices comprise: a platform (e.g., a sterile platform) comprising at least one of a magnetically-attractive material and a material capable of being magnetically-charged; an arm (e.g., a sterile arm) pivotally coupled to the platform such that the arm is rotatable around a rotational axis between a collapsed position and an expanded position; and a detent mechanism configured to adjustably fix the position of the arm relative to the platform. In some embodiments, the detent mechanism comprises a detent member coupled to one of the platform and the arm such that the detent member is biased in a bias direction toward the other of the platform and the arm. In some embodiments, the detent mechanism further comprises a spring configured to bias the detent member in the bias direction. In some embodiments, the detent member comprises a ball. In some embodiments, the platform comprises a resilient portion biased toward the arm, and the detent member comprises a protrusion extending from the resilient portion of the platform such that the detent member is biased in a bias direction toward the other of the platform and the arm. In some embodiments, the other of the platform and the arm comprises one or more indentations configured to receive the detent member. In some embodiments, the one or more indentations comprise a first indentation corresponding to the collapsed position of the arm and a second indentation corresponding to the expanded position of the arm. In some embodiments, the one or more indentations comprise a third indentation corresponding to at least one position of the arm between the collapsed position and the expanded position. In some embodiments, at least one of the one or more indentations comprises a curved surface. In some embodiments, at least one of the one or more indentations comprises a substantially semispherical surface. In some embodiments, the detent member of the detent mechanism is coupled to the platform, and the arm comprises the indentation. In some embodiments, the detent member of the detent mechanism is coupled to the arm, and the platform comprises the indentation. In some embodiments, the detent mechanism is configured such that the detent member can move linearly along a bias axis between an extended position and a collapsed position, In some embodiments, the bias axis is substantially perpendicular to the rotational axis. In some embodiments, the arm is rotatable in a rotational plane, and the bias axis is substantially parallel to the rotational plane. In some embodiments, the arm is rotatable in a rotational plane, and the bias axis is substantially perpendicular to the rotational plane.

Some embodiments of the present medical devices comprise: a platform; an arm pivotally coupled to the platform such that the arm is rotatable at least 90 degrees around a rotational axis between a collapsed position and an expanded position; a first gear coupled in fixed relation to the arm such that the rotational axis passes through the first gear; and a second gear rotatably coupled to the platform; where the medical device is configured such that: a tool can be coupled to the second gear such that the tool can be rotated to rotate the second gear; and if the second gear is rotated in a first rotational direction when the arm is in the collapsed position, then the arm will rotate from the collapsed position toward the expanded position. In some embodiments, the medical device is configured such that: if the second gear is rotated in a second rotational direction when the arm is in the expanded position, then the arm will rotate from the expanded position toward the collapsed position. In some embodiments, the second gear is configured to rotate around a first gear axis. In some embodiments, the arm is rotatable in a rotational plane, and the first gear axis is substantially parallel to the rotational plane. In some embodiments, the arm is rotatable in a rotational plane, and the first gear axis is substantially perpendicular to the rotational plane. Some embodiments further comprise: a third gear coupled to the first gear and the second gear such that if the second gear is rotated, the second gear will rotate the third gear and the third gear will rotate the first gear. In some embodiments, the third gear is configured to rotate around a second gear axis. In some embodiments, the second gear axis is substantially perpendicular to the first gear axis.

Some embodiments of the present medical devices comprise: a platform; an arm pivotally coupled to the platform such that the arm is rotatable around a rotational axis and in a rotational plane between a collapsed position and an expanded position; a first gear coupled in fixed relation to the arm such that the rotational axis passes through the first gear; a second gear rotatably coupled to the platform and configured to rotate around a first gear axis that is substantially perpendicular to the rotational axis of the arm and substantially parallel to the rotational plane of the arm; and a third gear coupled to the first gear and the second gear such that if the second gear is rotated, the second gear will rotate the third gear and the third gear will rotate the first gear; where the medical device is configured such that: a tool can be coupled to the second gear such that the tool can be rotated to rotate the second gear; and if the second gear is rotated in a first rotational direction when the arm is in the collapsed position, then the arm will rotate from the collapsed position toward the expanded position. In some embodiments, the platform comprises at least one of a magnetically-attractive material and a material capable of being magnetically-charged.

Some embodiments of the present medical devices comprise: a platform; an arm having a hub that is pivotally coupled to the platform such that the arm is rotatable at least 90 degrees around a rotational axis between a collapsed position and an expanded position; a threaded member rotatably coupled to the platform; a shuttle coupled to the threaded member; and a shuttle arm having a first end coupled to the shuttle and a second end coupled to the hub of the arm; where the medical device is configured such that: a tool can be coupled to the threaded member such that the tool can be rotated to rotate the threaded member; and if the threaded member is rotated in a first rotational direction when the arm is in the collapsed position, then the shuttle will travel in a substantially linear first direction to cause the arm to rotate from the collapsed position toward the expanded position. In some embodiments, the medical device is configured such that: if the threaded member is rotated in a second rotational direction when the arm is in the expanded position, then the shuttle will travel in a substantially linear second direction substantially opposite the first direction to cause the arm to rotate from the expanded position toward the collapsed position. In some embodiments, the threaded member is configured to rotate around a member axis. In some embodiments, the arm is rotatable in a rotational plane, and the member axis is substantially parallel to the rotational plane. In some embodiments, the platform comprises at least one of a magnetically-attractive material and a material capable of being magnetically-charged.

Some embodiments of the present medical devices comprise: a platform; an arm coupled to the platform with a pin slidably disposed within a cam slot defined within one of the platform and the arm, the pin being coupled to the other of the platform and the arm, the arm movable between an expanded position and a collapsed position; a threaded member rotatably coupled to the platform; and a shuttle coupled to the threaded member and pivotally coupled to the arm; where the medical device is configured such that: a tool can be coupled to the threaded member such that the tool can be rotated to rotate the threaded member; and if the threaded member is rotated in a first rotational direction when the arm is in the collapsed position, then the shuttle will travel in a substantially linear first direction to cause the arm to move from the collapsed position toward the expanded position. In some embodiments, the platform has length, a longitudinal axis, and a guide rod that is substantially parallel to the longitudinal axis. In some embodiments, the shuttle is slidably coupled to the guide rod. In some embodiments, the medical device is configured such that: if the threaded member is rotated in a first rotational direction when the arm is in the collapsed position, then the shuttle will travel in a substantially linear first direction along the guide rod to cause the arm to move from the collapsed position toward the expanded position. In some embodiments, the platform comprises at least one of a magnetically-attractive material and a material capable of being magnetically-charged.

Some embodiments of the present medical devices comprise: a platform; an arm pivotally coupled to the platform such that the arm is rotatable around a rotational axis between a collapsed position and an expanded position; and a spring configured to bias the arm toward the platform in a first direction that substantially parallel to the rotational axis; where the medical device is configured such that: in the absence of an external force the arm can contact the platform such that the arm is substantially prevented from rotating relative to the platform; a tool can be coupled to the arm to move the arm relative to the platform in a second direction that is substantially parallel to the rotational axis; and if the arm is moved in the second direction such that the arm is separated from the platform then the arm is permitted to rotate relative to the platform. In some embodiments, one of the platform and the arm comprises a tongue, the other of the platform and the arm comprises a groove, and the device is configured such that if the tongue is aligned with the groove and the arm contacts the platform, the tongue and groove cooperate to substantially prevent rotation of the arm relative to the platform. In some embodiments, the other of the platform and the arm comprises two grooves. In some embodiments, the two grooves intersect each other and the rotational axis. In some embodiments, the intersecting grooves are disposed at an angle of between 30 and 60 degrees relative to one another. In some embodiments, one of the two grooves corresponds to the collapsed position of the arm, and the other of the two grooves corresponds to the expanded position of the arm. In some embodiments, the platform comprises at least one of a magnetically-attractive material and a material capable of being magnetically-charged.

Some embodiments of the present medical devices comprise: a platform comprising a first set of teeth; an arm pivotally coupled to the platform such that the arm is rotatable around a rotational axis between a collapsed position and an expanded position, the arm comprising a second set of teeth; and a spring configured to bias one of the arm and the platform against the other of the arm and the platform; where the medical device is configured such that: in the absence of an external force, the first set of teeth contacts the second set of teeth such that the arm is substantially prevented from rotating relative to the platform; and a tool can be coupled to the medical device to rotate the arm around the rotational axis. In some embodiments, the platform comprises at least one of a magnetically-attractive material and a material capable of being magnetically-charged.

Some embodiments of the present medical devices comprise: a platform; an arm pivotally coupled to the platform such that the arm is rotatable at least 90 degrees around a rotational axis between a collapsed position and an expanded position; a motor coupled to the arm; a first gear coupled in fixed relation to the platform; and a second gear coupled to the motor; where the medical device is configured such that: if the motor is actuated to rotate the second gear in a first rotational direction when the arm is in the collapsed position, then the arm will rotate from the collapsed position toward the expanded position. Some embodiments further comprise: a third gear rotatably coupled to the platform such that the third gear is configured to rotate around the rotational axis. In some embodiments, the platform comprises at least one of a magnetically-attractive material and a material capable of being magnetically-charged.

Some embodiments of the present medical devices comprise: a platform; an arm having a hub that is pivotally coupled to the platform such that the arm is rotatable at least 90 degrees around a rotational axis between a collapsed position and an expanded position; a member movably coupled to the platform; a shuttle coupled to the member; and a shuttle arm having a first end coupled to the shuttle and a second end coupled to the hub of the arm; where the medical device is configured such that: a tool can be coupled to the member to move the member; and if the member is moved in a substantially linear first direction when the arm is in the collapsed position, then the shuttle will travel in the first direction to cause the arm to rotate from the collapsed position toward the expanded position. Some embodiments further comprise: a spring configured to bias the member is a second direction that is substantially opposite the first direction such that if the arm is deployed and the member is moved in the second direction, the spring will cause the arm to rotate toward the collapsed position. In some embodiments, the platform comprises at least one of a magnetically-attractive material and a material capable of being magnetically-charged.

In some embodiments, the platform comprises a magnetically-attractive material. In some embodiments, the magnetically-attractive material includes a magnet. In some embodiments, the magnetically-attractive material includes two magnets. In some embodiments, the platform has a coupling side; each magnet has an N pole and an S pole; and the N pole of one magnet is oriented toward the coupling side, and the S pole of the other magnet is oriented toward the coupling side. In some embodiments, when the arm is in the collapsed position, the device is at least partially defined by a maximum transverse perimeter that is less than about 7 inches. In some embodiments, the area circumscribed by the maximum transverse perimeter is less than about 3.2 square inches.

In some embodiments, the platform is at least partially defined by a maximum transverse perimeter, and the platform has a longitudinal recess; the arm has a central longitudinal axis; and when the arm is in the collapsed position, the central longitudinal axis of the arm passes through the maximum transverse perimeter of the platform.

Any embodiment of any of the present systems, apparatuses, devices, and methods can consist of or consist essentially of—rather than comprise/include/contain/have—any of the described elements and/or features. Thus, in any of the claims, the term "consisting of" or "consisting essentially of" can be substituted for any of the open-ended linking verbs recited above, in order to change the scope of a given claim from what it would otherwise be using the open-ended linking verb.

Details associated with the embodiments described above and others are presented below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers.

FIG. 1 depicts a graphical representation of one of the present medical devices positioned within a body cavity of a patient and magnetically coupled to a positioning apparatus that is located outside the cavity.

FIG. 2 is an end view of the medical device and positioning apparatus shown in FIG. 1.

FIGS. 4A-4H depict various views of one embodiment of the present medical devices.

FIGS. 5A-5E depict various views of another embodiment of the present medical devices.

FIGS. 6A-6E depict various views of another embodiment of the present medical devices.

FIGS. 10A-10E depict various views of another embodiment of the present medical devices.

FIGS. 18A-18J depict various views of another embodiment of the present medical devices.

FIGS. 19A-19K depict various views of another embodiment of the present medical devices.

FIGS. 22A-22E depict various views of another embodiment of the present medical devices.

FIGS. 24A-24F depict various views of another embodiment of the present medical devices.

DESCRIPTION OF ILLUSTRATIVE EMBODIMENTS

Figure 3A:
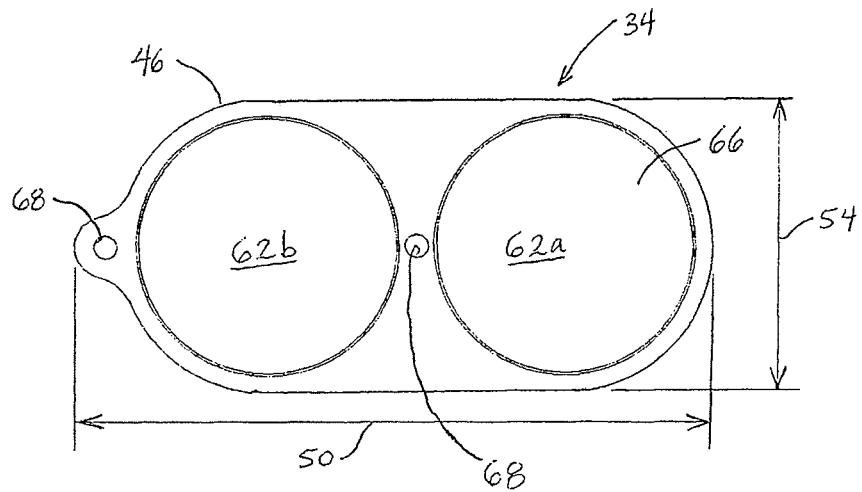
FIGS. 3A and 3B are bottom and side-cross-sectional views, respectively, of one of the present positioning apparatuses.

The term "coupled" is defined as connected, although not necessarily directly, and not necessarily mechanically; two items that are "coupled" may be integral with each other. The terms "a" and "an" are defined as one or more unless this disclosure explicitly requires otherwise. The term "substantially" is defined as being largely but not necessarily wholly what is specified, as understood by a person of ordinary skill in the art. For example, in any of the present embodiments, the term "substantially" may be substituted with "within [a percentage] of" what is specified, where the percentage includes any of 5, 10, and/or 15 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a system, medical device, or apparatus that "comprises," "has," "includes" or "contains" one or more elements possesses those one or more elements, but is not limited to possessing only those one or more elements. Likewise, an element of a system, medical device, or apparatus that "comprises," "has," "includes" or "contains" one or more features possesses those one or more features, but is not limited to possessing only those features. For example, a medical device that comprises a platform and a magnetically-attractive material includes the specified features but is not limited to having only those features. Such a medical device could also include, for example, an arm coupled to the platform.

Further, a device or structure that is configured in a certain way is configured in at least that way, but it can also be configured in other ways than those specifically described.

Referring now to the drawings, shown in FIGS. 1 and 2 by reference numeral 10 is one embodiment of a system for medical procedures that can be used with the present invention. System 10 is shown in conjunction with a patient 14, and more particularly in FIG. 1 is shown relative to a longitudinal cross-sectional view of the ventral cavity 18 of a human patient 14, and in FIG. 2 is shown relative to a transverse cross-sectional view of the ventral cavity of the patient. For brevity, cavity 18 is shown in simplified conceptual form without organs and the like. Cavity 18 is at least partially defined by wall 22, such as the abdominal wall, that includes an interior surface 26 and an exterior surface 30. The exterior surface 30 of wall 22 can also be an exterior surface 30 of the patient 14. Although patient 14 is shown as human in FIGS. 1 and 2, various embodiments of the present invention (including the version of system 10 shown in FIGS. 1 and 2) can also be used with other animals, such as in veterinary medical procedures.

Further, although system 10 is depicted relative to ventral cavity 18, system 10 and various other embodiments of the present invention can be utilized in other body cavities of a patient, human or animal, such as, for example, the thoracic cavity, the abdominopelvic cavity, the abdominal cavity, the pelvic cavity, and other cavities (e.g., lumens of organs such as the stomach, colon, or bladder of a patient). In some embodiments of the present methods, and when using embodiments of the present devices and systems, a pneumoperitoneum may be created in the cavity of interest to yield a relatively-open space within the cavity.

As shown in FIGS. 1 and 2, system 10 comprises an apparatus 34 and a medical device 38; the apparatus is configured to magnetically position the device with a body cavity of a patient. In some embodiments, apparatus 34 can be described as an exterior apparatus and/or external unit and device 38 as an interior device and/or internal unit due the locations of their intended uses relative to patients. As shown, apparatus 34 can be positioned outside the cavity 18 near, adjacent to, and/or in contact with the exterior surface 30 of the patent 14. Device 38 is positionable (can be positioned), and is shown positioned, within the cavity 18 of the patient 14 and near, adjacent to, and/or in contact with the interior surface 26 of wall 22. Device 38 can be inserted or introduced into the cavity 18 in any suitable fashion. For example, the device 18 can be inserted into the cavity through a puncture (not shown) in wall 22, through a tube or trocar (not shown) extending into the cavity 18 through a puncture or natural orifice (not shown), or may be inserted into another portion of the patient 14 and moved into the cavity 18 with apparatus 34, such as by the methods described in this disclosure. If the cavity 18 is pressurized, device 38 can be inserted or introduced into the cavity 18 before or after the cavity 18 is pressurized.

Additionally, some embodiments of system 10 include a version of device 38 that has a tether 42 coupled to and extending away from the device 38. In the depicted embodiment, tether 42 extends from device 38 and out of the cavity 18, for example, through the opening (not shown) through which device 38 is introduced into the cavity 18. The tether 42 can be flexible and/or elongated. In some embodiments, the tether 42 can include one or more conduits for fluids that can be used, for example, for actuating a hydraulic cylinder or irrigating a region within the cavity 18. In some embodiments, the tether 42 can include one or more conductors for enabling electrical communication with the device 38. In some embodiments, the tether 42 can include one or more conduits for fluid and one or more conductors. In some embodiments, the tether does not include a conduit or conductor and, instead, includes a cord for positioning, moving, or removing device 38 from the cavity 18. The tether 14, for example, can be used to assist in positioning the device 34 while the device 34 is magnetically coupled to the apparatus 38, or to remove the device 34 from the cavity 18 when device 38 is not magnetically coupled to apparatus 34.

As is discussed in more detail below, apparatus 34 and device 38 can be configured to be magnetically couplable to one another such that device 38 can be positioned or moved within the cavity 18 by positioning or moving apparatus 34 outside the cavity 18. "Magnetically couplable" means capable of magnetically interacting so as to achieve a physical result without a direct physical connection. Examples of physical results are causing device 38 to move within the cavity 18 by moving apparatus 34 outside the cavity 18, and causing device 38 to remain in a position within the cavity 18 or in contact with the interior surface 26 of wall 22 by holding apparatus 34 in a corresponding position outside the cavity 18 or in contact with the exterior surface 30 of wall 22. Magnetic coupling can be achieved by configuring apparatus 34 and device 38 to cause a sufficient magnetic attractive force between them. For example, apparatus 34 can comprise one or more magnets (e.g., permanent magnets, electromagnets, or the like) and device 38 can comprise a ferromagnetic material. In some embodiments, apparatus 34 can comprise one or more magnets, and device 38 can comprise a ferromagnetic material, such that apparatus 34 attracts device 38 and device 38 is attracted to apparatus 34. In other embodiments, both apparatus 34 and device 38 can comprise one or more magnets such that apparatus 34 and device 38 attract each other.

The configuration of apparatus 34 and device 38 to cause a sufficient magnetic attractive force between them can be a configuration that results in a magnetic attractive force that is large or strong enough to compensate for a variety of other factors (such as the thickness of any tissue between them) or forces that may impede a desired physical result or desired function. For example, when apparatus 34 and device 38 are magnetically coupled as shown, with each contacting a respective surface 26 or 30 of wall 22, the magnetic force between them can compress wall 22 to some degree such that wall 22 exerts a spring or expansive force against apparatus 34 and device 38, and such that any movement of apparatus 34 and device 38 requires an adjacent portion of wall 22 to be similarly compressed. Apparatus 34 and device 38 can be configured to overcome such an impeding force to the movement of device 38 with apparatus 34. Another force that the magnetic attractive force between the two may have to overcome is any friction that exists between either and the surface, if any, that it contacts during a procedure (such as apparatus 34 contacting a patient's skin). Another force that the magnetic attractive force between the two may have to overcome is the force associated with the weight and/or tension of the tether 42 and/or frictional forces on the tether 42 that may resist, impede, or affect movement or positioning of device 38 using apparatus 34.

In some embodiments, device 38 can be inserted into cavity 18 through an access port having a suitable internal diameter. Such access ports includes those created using a conventional laparoscopic trocar, gel ports, those created by incision (e.g., abdominal incision), and natural orifices. Device 38 can be pushed through the access port with any elongated instrument such as, for example, a surgical instrument such as a laparoscopic grasper or a flexible endoscope.

In embodiments where the tether 42 is connectable to a power source or a hydraulic source (not shown), the tether can be connected to the power source or the hydraulic source (which may also be described as a fluid source) either before or after it is connected to device 38.

In some embodiments, when device 38 is disposed within cavity 18, device 38 can be magnetically coupled to apparatus 34. This can serve several purposes including, for example, to permit a user to move device 38 within cavity 18 by moving apparatus 34 outside cavity 18. The magnetic coupling between the two can be affected by a number of factors, including the distance between them. For example, the magnetic attractive force between device 38 and apparatus 34 increases as the distance between them decreases. As a result, in some embodiments, the magnetic coupling can be facilitated by temporarily compressing the tissue (e.g., the abdominal wall) separating them. For example, after device 38 has been inserted into cavity 18, a user (such as a surgeon) can push down on apparatus 34 (and wall 22) and into cavity 18 until apparatus 34 and device 38 magnetically couple.

In FIGS. 1 and 2, apparatus 34 and device 38 are shown at a coupling distance from one another and magnetically coupled to one another such that device 38 can be moved within the cavity 18 by moving apparatus 34 outside the outside wall 22. The "coupling distance" between two structures (e.g., apparatus 34 and device 38) is defined as a distance between the closest portions of the structures at which the magnetic attractive force between them is great enough to permit them to function as desired for a given application.

Figure 3B:
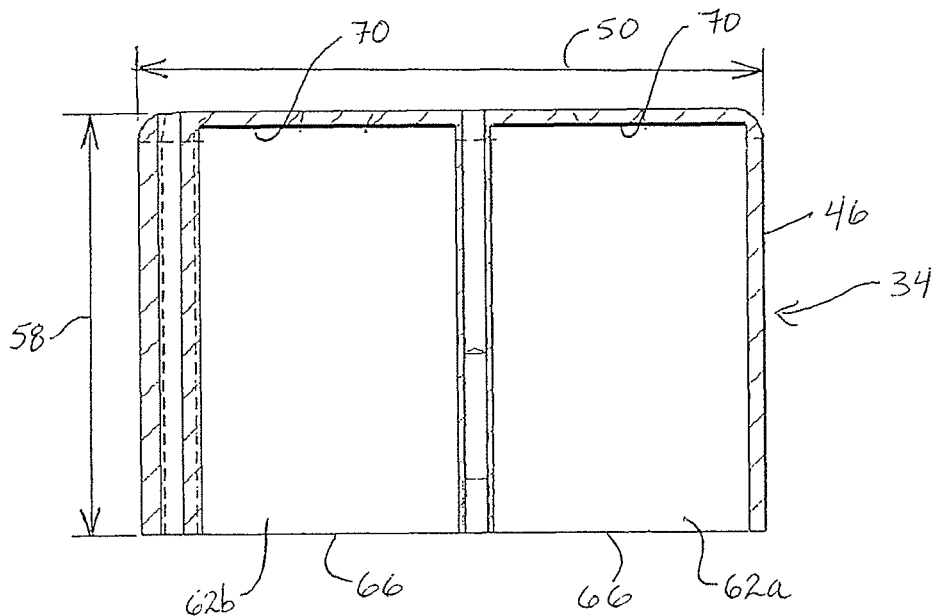

Referring now to FIGS. 3A and 3B, a bottom view and a side cross-sectional view are shown, respectively, of an embodiment of apparatus 34. Apparatus 34 has a width 50, a depth 54, and a height 58, and includes a housing 46. The apparatus (and, more specifically, housing 46) is configured to support, directly or indirectly, at least one magnetic assembly in the form of one or more magnetic field sources. In the embodiments shown, apparatus 34 is shown as including a first magnetic field source 62a and a second magnetic field source 62b. Each magnetic field source 62a, 62b has a coupling end 66 and a distal end 70. As described in more detail below, the coupling ends face device 38 when apparatus 34 and device 38 are magnetically coupled. The depicted embodiment of housing 46 of apparatus 34 also includes a pair of guide holes 68 extending through housing 46 for guiding, holding, or supporting various other devices or apparatuses, as described in more detail below. In other embodiments, the housing of apparatus 34 can have any other suitable number of guide holes 68 such as, for example, zero, one, three, four, five, or more guide holes 68. In some embodiments, housing 46 comprises a material that is minimally reactive to a magnetic field such as, for example, plastic, polymer, fiberglass, or the like. In other embodiments, housing 46 can be omitted or can be integral with the magnetic field sources such that the apparatus is, itself, a magnetic assembly comprising a magnetic field source.

Magnets, in general, have a north pole (the N pole) and a south pole (the S pole). In some embodiments, apparatus 34 can be configured (and, more specifically, its magnetic field sources can be configured) such that the coupling end 66 of each magnetic field source is the N pole and the distal end 70 of each magnetic field source is the S pole. In other embodiments, the magnetic field sources can be configured such that the coupling end 66 of each magnetic field source is the S pole and the distal end 70 of each magnetic field source is the N pole. In other embodiments, the magnetic field sources can be configured such that the coupling end of the first magnetic field source 62a is the N pole and the recessed end of the first magnetic field source 62a is the S pole, and the coupling end of the second magnetic field source 62b is the S pole and the recessed end of the second magnetic field source 62b is the N pole. In other embodiments, the magnetic field sources can be configured such that the coupling end of the first magnetic field source 62a is the S pole and its recessed end is the N pole, and the coupling end of the second magnetic field source 62b is the N pole and its recessed end is the S pole.

In the embodiment shown, each magnetic field source includes a solid cylindrical magnet having a circular cross section. In other embodiments, each magnetic field source can have any suitable cross-sectional shape such as, for example, rectangular, square, triangular, fanciful, or the like. In some embodiments, each magnetic field source comprises any of: any suitable number of magnets such as, for example, one, two, three, four, five, six, seven, eight, nine, ten, or more magnets; any suitable number of electromagnets such as, for example, one, two, three, four, five, six, seven, eight, nine, ten or more electromagnets; any suitable number of pieces of ferromagnetic material such as, for example, one, two, three, four, five, six, seven, eight, nine, ten or more pieces of ferromagnetic material; any suitable number of pieces of paramagnetic material such as, for example, one, two, three, four, five, six, seven, eight, nine, ten or more pieces of paramagnetic material; or any suitable combination of magnets, electromagnets, pieces of ferromagnetic material, and/or pieces of paramagnetic material.

In some embodiments, each magnetic field source can include four cylindrical magnets (not shown) positioned in end-to-end in linear relation to one another, with each magnet having a height of about 0.5 inch and a circular cross-section that has a diameter of about 1 inch. In these embodiments, the magnets can be arranged such that the N pole of each magnet faces the S pole of the next adjacent magnet such that the magnets are attracted to one another and not repulsed.

Examples of suitable magnets can include: flexible magnets; Ferrite, such as can comprise Barium or Strontium; AlNiCo, such as can comprise Aluminum, Nickel, and Cobalt; SmCo, such as can comprise Samarium and Cobalt and may be referred to as rare-earth magnets; and NdFeB, such as can comprise Neodymium, Iron, and Boron. In some embodiments, it can be desirable to use magnets of a specified grade, for example, grade 40, grade 50, or the like. Such suitable magnets are currently available from a number of suppliers, for example, Magnet Sales & Manufacturing Inc., 11248 Playa Court, Culver City, Calif. 90230 USA; Amazing Magnets, 3943 Irvine Blvd. #92, Irvine, Calif. 92602; and K & J Magnetics Inc., 2110 Ashton Dr. Suite 1A, Jamison, Pa. 18929. In some embodiments, one or more magnetic field sources can comprise ferrous materials (e.g., steel) and/or paramagnetic materials (e.g., aluminum, manganese, platinum).

FIGS. 4A-4H depict various views of device 38a, another embodiment of one of the present medical devices that can be moved within a body cavity using one of the present apparatuses to which it is magnetically coupled, and which can also be used as part of one of the present systems. In embodiments of the present medical devices and systems in which the medical device (e.g., devices 38a, 38b, 38c, 38d, 38e, 38f, 38g, 38h, 38i, 38j, 38k, 38l, 38m, 38n, 38o, 38p, 38q, 38r, 38s, 38t, and 38u) includes an arm, a tool, a light emitting diode (LED), or the like that is coupled to the structure shown, for example, in FIGS. 4A-4H, that structure may be referred to as a "platform."

Figure 4F:
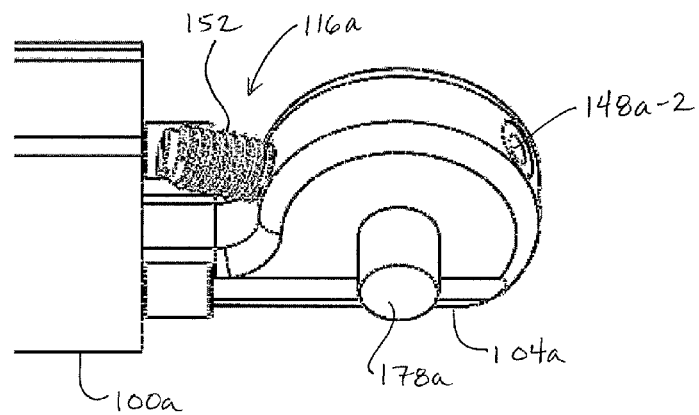
Figure 4G:
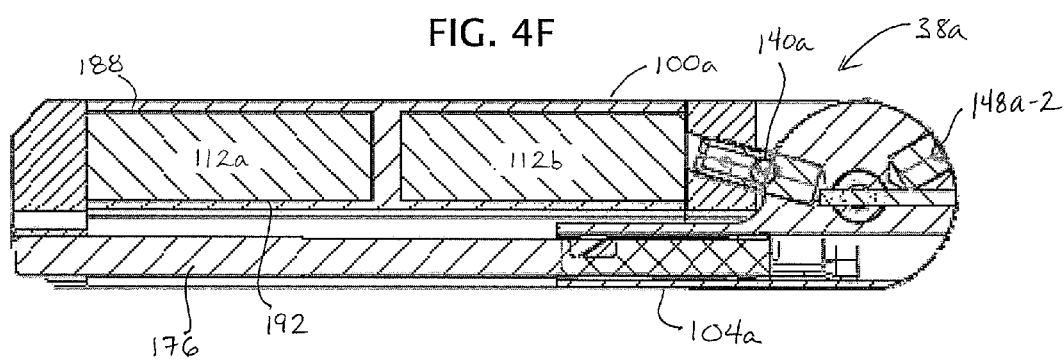
Figure 4H:
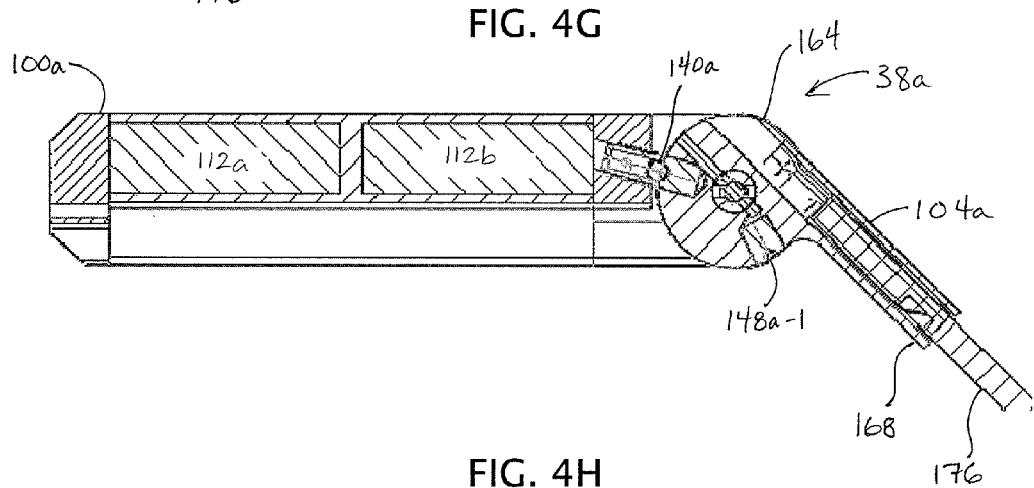

In the embodiment shown, device 38a comprises: a platform 100a and an arm 104a pivotally coupled to platform 100a such that arm 104a is rotatable around a rotational axis 108 between a collapsed position (FIG. 4G) and an expanded position (FIG. 4H). In the embodiment shown, platform 100a comprises at least one of a magnetically-attractive material and a material capable of being magnetically-charged (e.g., comprises members 112a, 112b that each comprises a magnetically-attractive material and/or a material that is capable of being magnetically charged). In the embodiment shown, device 38a also comprises a detent mechanism 116a configured to adjustably fix the position of arm 104a relative to platform 100a. FIG. 4E is a partially cross-sectional view, and FIG. 4F is a partially cutaway view that omits a portion of platform 100a to show portions of device 38a in more detail.

As shown, platform 100a can comprise a housing 120a and can support one or more members 112a, 112b, as noted above. Platform 100a has a proximal end 122, a distal end 124, and a length 128 extending between proximal end 122 and distal end 124. Platform 100a also has, in the depicted embodiment, a longitudinal recess 132 defined along at least a portion of length 128 of the platform. As shown in FIGS. 4B and 4D, platform 100a can also have a maximum transverse perimeter 136. The "maximum transverse perimeter" of one of the present platforms is defined by the smallest circle or rectangle that can circumscribe the largest cross-section of the platform. In some embodiments, when arm 104a is in the collapsed position, the maximum transverse perimeter is less than about 7 inches. In some embodiments, the area circumscribed by the maximum transverse perimeter is less than about 3.2 square inches.

In the embodiment shown, detent mechanism 116a comprises a detent member 140a coupled to one of the platform and the arm such that detent member 140a is biased in a bias direction 144a toward the other of the platform and the arm. In the embodiment shown, the other of the platform and the arm comprises one or more indentations 148a configured to receive detent member 140a. For example, in the embodiment shown, detent member 140a is coupled to platform 100a and biased toward arm 104a which comprises indentations (e.g., 148a-1, 148a-2). In other embodiments, detent member 140a can be coupled to arm 104a and biased toward platform 100a (e.g., platform 100a can comprise one or more indentations). In the embodiment shown, detent mechanism 116a further comprises a spring 152 configured to bias detent member 140a in bias direction 144a. In the embodiment shown, detent member 112a comprises a ball. In the embodiment shown, the one or more indentations comprise a first indentation 148a-1 corresponding to the collapsed position of the arm (FIG. 4G) and a second indentation 14a-2 corresponding to the expanded position of the arm (FIG. 4H). In some embodiments, the one or more indentations comprise a third indentation (not shown) corresponding to at least one position of the arm between the collapsed position and the expanded position. In the embodiment shown, at least one (e.g., each) of the one or more indentations 148a-1, 148a-2 comprises a curved surface 156. For example, in the embodiment shown, at least one (e.g., each) of indentations 148a-1, 148a-2 comprises surface 156 that is semispherical (a portion of a sphere that is less than a hemisphere—less then one half of a sphere).

In the embodiment shown, detent mechanism 116a is configured such that detent member 140a moves linearly along a bias axis 160 between an extended position (e.g., FIGS. 4G and 4H) and a collapsed position (e.g., when arm 104a is between the collapsed position and the expanded position such that spring 152 is compressed and detent member 140a is correspondingly depressed). In the embodiment shown, bias axis 160a is substantially perpendicular to rotational axis 108. In the embodiment shown, arm 104a is rotatable in a rotational plane (passing through substantially the center of platform 100a and of arm 104a such that the rotational plane passes through substantially the center of arm 104a in both of the expanded and collapsed positions), and bias axis 160a is substantially parallel to the rotational plane.

Arm 104a can have a proximal end 164 and a distal end 168. Arm 104a can be coupled to platform 100a such that arm 104a is movable between (1) a collapsed position where distal end 164 of arm 104a is adjacent to platform 100a, or where arm 104a is substantially parallel to platform 100a, as shown in FIG. 4H, and (2) an expanded position where distal end 168 of arm 104a is spaced apart from platform 100a, or where arm 104a is oriented at a non-zero angle to platform 100a. When arm 104a is in the collapsed position, the longitudinal axis of arm 104a is preferably disposed within maximum transverse perimeter 136 of platform 100a. Similarly, when arm 104a is in the collapsed position, at least a portion of the arm can be disposed within recess 132 such that a majority of the lateral sides of arm 104a is bordered by platform 100a such that platform 100a affords some protection to arm 104a during, for example, insertion into and removal from cavity 18.

As best shown in FIG. 4D, arm 104a can include an opening and/or connector 172 configured to be coupled to a tool (not shown—e.g., a hook or other mechanical implement) and/or a tether (e.g., tether 42), such as, for example, to permit a user to apply a mechanical force to rotate the arm from the collapsed position to the expanded position, or from the expanded position to the collapsed position; and/or to couple the tether to the arm to deliver power or control signals or forces to actuate or operate a tool 176 coupled to the arm. Tool 176 can include, for example, a blade, a hook, a cautery tool, or any other tool that may be useful or advantageous for a medical procedure. In the embodiment shown, tool 176 is a cautery tool. Cautery tool 176 can be coupled to arm 104a, for example, at or near the distal end 168 of the arm. Cautery tool 176 can be powered by way of a conductor (not shown) that runs through, with, or along the tether 42. Furthermore, during use of device 38a, the conductor can be positioned in and/or coupled to opening and/or connector 172 located in the proximal end 164 of the arm and visible, for example, in FIGS. 4D, 4G, and 4H. In some embodiments, cautery tool 176 can be positively charged with a high electric voltage, such as, for example, a voltage that is compatible with known electrosurgical units (e.g., up to 9,000 Volts peak-to-peak and/or 390 kHz sinusoidal), such that when cautery tool 176 contacts a grounded patient's flesh or tissue, the circuit completes and cautery tool 176 is able to cut or cauterize the flesh or tissue with relatively little force. When arm 104a is in the collapsed position, the longitudinal axis of cautery tool 176, or another tool 176, can be parallel to the longitudinal axis of arm 104a and can also be within the maximum transverse perimeter of platform 100a. In the embodiment shown, device 38a is configured such that a tool (e.g., a tool 220) can be coupled to arm 104a (e.g., via axle 178a with an Allen screw head) such that the tool can be rotated to rotate arm 104a from the collapsed position toward the expanded position In some embodiments, device 38a can be inserted into cavity 18 and magnetically coupled to apparatus 34, as described above. Once device 38a and apparatus 34 are magnetically coupled to each other, or device 38a is otherwise secured in position within cavity 18, a user can deploy or expand the tool (e.g., cautery tool 176) from the collapsed position (e.g., FIGS. 4A, 4C, and 4G) to an expanded position (e.g. FIG. 4H) by applying a mechanical force (e.g., via an external tool or tether 42) to rotate arm 104a relative to body 100a. In some embodiments, when arm 104a is in an expanded position, the user can move device 38a to adjust its position within cavity 18 by moving magnetically coupled apparatus 34 outside cavity 18. In some embodiments, the user may further be able to move or adjust the pitch and yaw of device 38a by, for example, moving or adjusting the pitch and yaw of apparatus 34 where wall 22 is compliant enough to permit such pitch and yaw motion or adjustment. Embodiments of the present devices and systems can be configured such that when device 38a is in an operational position (e.g., cautery tool 176 is in a position that is acceptable to the user for performing a task within cavity 18), cautery tool 176 can be activated or electrified in any suitable manner, including, for example, through an electrosurgery unit (with or without a foot pedal), a power source, or the like. Embodiments of the present devices and systems can be configured such that cautery tool 176 can be powered and actuated by conventional methods and systems such as, for example, with a conventional cautery power supply. Such a power supply can be electrically-coupled to or in electrical communication with the cautery tool 176 in any suitable manner, including, for example, by way of a physical tether (e.g., tether 42). Embodiments of the present devices and systems can be configured such that a user can activate cautery tool 176 using a foot pedal, a switch, a voice-actuated activator, or any other suitable method, system, or device. Other embodiments of the present devices and systems can be configured such that cautery tool 176 can be deployed (e.g., arm 104a can be deployed from a collapsed to an expanded position) and/or controlled by way of a joystick or other relatively more-complicated user interface.

In the embodiment shown, platform 100a includes housing 120a and two magnetically-attractive or magnetically-chargeable members (in this case, first member 112a and second member 112b), which are supported by (e.g., coupled to) housing 120a. Device 38a has a coupling side 180 and a working side 184. Device 38a can be part of embodiments of the present systems that include an embodiment of apparatus 34. Device 38a can be configured such that coupling side 180 faces an embodiment of apparatus 34, and such that working side 184 faces away from apparatus 34, when apparatus 34 and device 38a are magnetically coupled to each other. Housing 120a can support or hold members 112a and 112b in fixed relation to one another. Each member has a coupling end 188 oriented toward coupling side 180 of device 38a and a distal end 192 oriented toward working side 180 of device 38a.

Members 112a and 112b can comprise any suitable material that is magnetically attracted to the magnetic field sources 62a, 62b of apparatus 34. Examples of such material include, for example, a magnet, a ferromagnetic material, and a paramagnetic material. In a further example, such material may include a permanent magnet material that can be magnetized and/or de-magnetized with exposure to a magnetic field. In some embodiments, one or both of apparatus 34 and device 38a are configured such that that the magnetic field sources of the apparatus can each be aligned with a different magnetically-attractive member of device 38a, meaning that an axis can be substantially centered in and run lengthwise through a given aligned pair comprising a magnetic field source of the apparatus and a magnetically-attractive member of the device. In the embodiment shown, members 112a and 112b each has an elongated shape. In some embodiments of the present devices, each member 112a, 112b comprises a cylindrical magnet having a height of about 0.25 inches, and a circular cross-section with a diameter of about 0.375 inches. In other embodiments, each member comprise a cylindrical magnet having a height of about any of 0.15 inches, 0.16 inches, 0.17 inches, 0.18 inches, 0.19 inches, 0.20 inches, or 0.21 inches; and a circular cross-section with a diameter of about any of: 0.25 inches, 0.3 inches, 0.35 inches, 0.375 inches, 0.4 inches, 0.45 inches, 0.5 inches, 0.55 inches, 0.6 inches, 0.625 inches, or 0.65 inches. In some embodiments, each member 112a, 112b comprises a plurality of magnets of varying sizes or shapes, for example, five cylindrical magnets having a circular cross-section, two with a height of about 0.6 inches and a diameter of about 0.375 inches, and three with a height of about 0.6 inches and a diameter of about 0.5 inches; four cylindrical magnets having a circular cross section, one with a height of about 0.06 inches and a diameter of about 0.5 inches, and three with a height of about 0.6 inches and a diameter of about 0.625 inches. In other embodiments, members 112a, 112b include any suitable cross-sectional shape, dimension, or number of magnets, or volumes of ferromagnetic or paramagnetic materials.

In embodiments of the present devices (e.g., device 38a), where members 112a and 112b include magnets, each member will generally have an N pole and an S pole. In some of these embodiments, first member 112a has its N pole oriented toward coupling end 188 and its S pole oriented toward distal end 192, and second member 112b has its S pole oriented toward its coupling end 188 and its N pole oriented toward its distal end 192, such that the members 112a, 112b are in an N-S/S-N configuration. In others of these embodiments, first member 112a has its S pole oriented toward coupling end 188 and its N pole oriented toward distal end 192, and second member 112b has its N pole oriented toward its coupling end 188 and its S pole oriented toward its distal end 192, such that the members 112a, 112b are in an S-N/N-S configuration.

For example, FIG. 1 depicts a pictorial side view of an embodiment of system 10 in which apparatus 34 and device 38 are magnetically coupled across a wall 22 of a patient with wall 22 shown in cross-section for clarity. As described above, the magnetic field sources 62a, 62b of apparatus 34 and the magnetically-attractive members 112a, 112b of device 38 (e.g., 38a) can be configured in various ways. In one "consistent" configuration, the coupling ends 66 of both magnetic field sources 62a, 62b are configured to have the same polarity (e.g., both N poles or both S poles), such that the coupling ends 66 of the magnetic field sources 62a, 62b have an N-N configuration or orientation or an S-S configuration or orientation. In this "consistent" configuration, device 38 can be configured such that members 112a, 112b are magnets and coupling ends 188 of members 112a, 112b are oppositely oriented relative to coupling ends 66 of magnetic field sources 62. For example, where coupling ends 66 of the field sources 62a, 62b have an N-N configuration, members 112a, 112b of the device can have an S-S configuration, and where coupling ends 66 have an S-S configuration, coupling ends 188 can have an N-N configuration. In this way, magnetic field sources 62a, 62b and members 112a, 112b will be attracted to, and attract, each other such that the magnetic attractive forced can be maximized between apparatus 34 and device 38.

In another "alternating" configuration, coupling ends 66 of magnetic field sources 62a, 62b can be configured to have different polarities. For example, the N pole of first magnetic field source 62a can be oriented at coupling end 66 while the S pole of second magnetic field source 62b can be oriented at its coupling end 66, or vice versa, such that the coupling ends of the magnetic field sources have an N-S or S-N configuration. In this "alternating" configuration, device 38 can be configured such that members 112a, 112b are magnets that also have an alternating orientation. For example, coupling ends 188 of members 112a, 112b can have an N-S orientation or an S-N orientation. In this way, the coupling end 66 with an N pole primarily attracts and is attracted to the coupling end 188 having an S pole, and the coupling end 66 with an S pole primarily attracts and is attracted to the coupling end 188 having an N pole. Stated otherwise, each coupling end 66 attracts and is attracted to the coupling end 188 having an opposite polarity, and each coupling end 66 repels and is repelled by the coupling end 188 having a like polarity. As such, when in the "alternating" configuration, apparatus 34 and device 38 are attracted to one another in a specific relationship, such that when apparatus 34 and device 38 are magnetically coupled, control over or "tracking" of device 38 can be improved.

FIGS. 5A-5E depict various views of another embodiment 38b of the present medical devices, which can also be used as part of one of the present systems. Medical device 38b is similar in several respects to medical device 38a, so generally only the differences between them will be described here. In particular, detent mechanism 116b comprises two detent members 140b-1, 140b-2 that are coupled to arm 104a and biased toward platform 100a which comprises indentations (e.g., 148b-1, 148b-2). In the embodiment shown, each bias axis 160b-1, 160b-2 is substantially perpendicular to rotational axis 108. In the embodiment shown, each bias axis 160b-1, 160b-2 is substantially perpendicular to the rotational plane of arm 104b. FIG. 5D is a partially cross-sectional view, and FIG. 5E is a partially cutaway view that omits a portion of platform 100b to show portions of device 38b in more detail. As illustrated, indentations 148b-1, 148b-2 can be defined by members 196b-1, 196b-2, respectively that can be disposed in platform 100b (e.g., in housing 116b). In other embodiments, indentations 196b-1, 196b-2 can be defined directly by housing 120b.

FIGS. 6A-6E depict various views of another embodiment 38c of the present medical devices, which can also be used as part of one of the present systems. Medical device 38c is similar in several respects to medical devices 38a and 38b, so generally only the differences between them will be described here. In particular, platform 100c comprises a resilient portion 200 (at or including a portion of distal end 124 of platform 100c and on only one side of arm 104c) biased toward arm 104c (if resilient portion 200 is deflected away from arm 104c, resilient portion 200 will tend to return to its pre-deflected or original position). Additionally, in the embodiment shown, detent member 140c comprises a protrusion extending from resilient portion 200 of platform 100c such that detent member 140c is biased in a bias direction 144c toward the arm. In this embodiment, as in device 38a, arm 104c includes first and second (a first set of) indentations 148c-1, 148c-2 corresponding to the collapsed position of the arm, and third and fourth (a second set of) indentations 148c-3, 148c-4 corresponding to the expanded position of the arm. FIG. 6D is a perspective view of the platform without the arm, and FIG. 6E is a partially cutaway view that omits a portion of platform 100c to show portions of device 38c in more detail. As shown, in some embodiments of the present medical devices, the arm (e.g., 104c) can be disposed on an axle 204c that is pivotally coupled to the platform (e.g., 100c) and/or a pin 208 can extend through arm 104c and into (and/or through) axle 204c to substantially fix the position of the arm relative to the axle. In the embodiment shown, resilient portion 200 is configured to act similarly to spring 152 in devices 38a, 38b to bias protrusions 140c-1, 140c-2 toward arm 104c. In some embodiments, resilient portion 200 can be purposefully weakened to permit it to act as described (e.g., platform 100c can be provided with notches, grooves, or the like at or around resilient portion 200 to permit resilient portion to function as described).

Figure 7A:
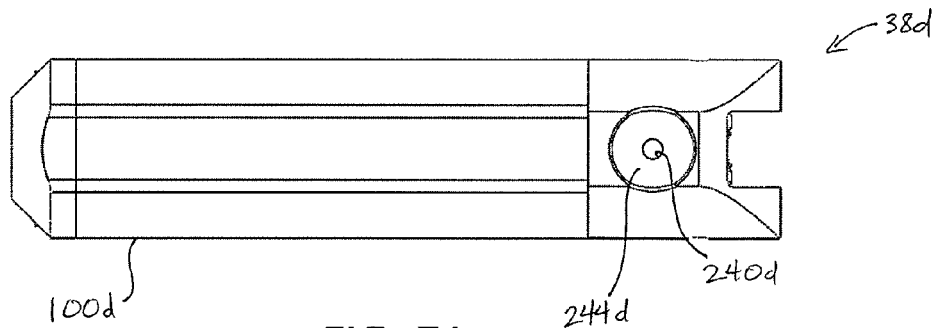
FIGS. 7A-7G depict various views of another embodiment of the present medical devices.
Figures 7B, 7C:
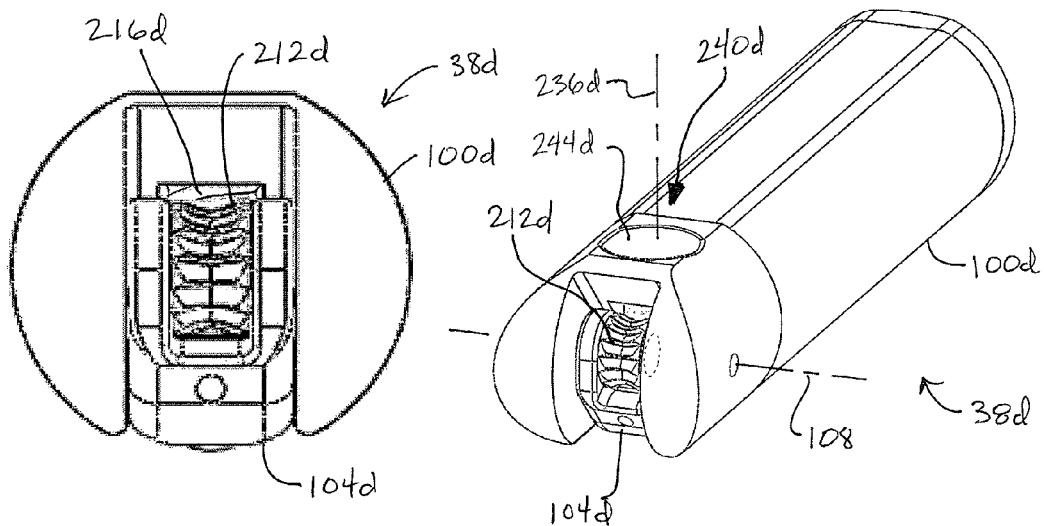
Figure 7D:
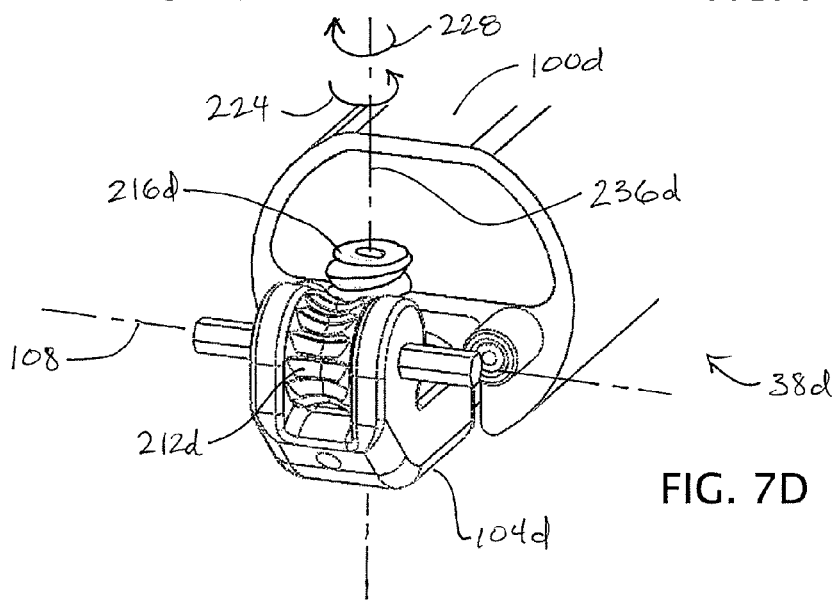
Figures 7E, 7F, 7G:
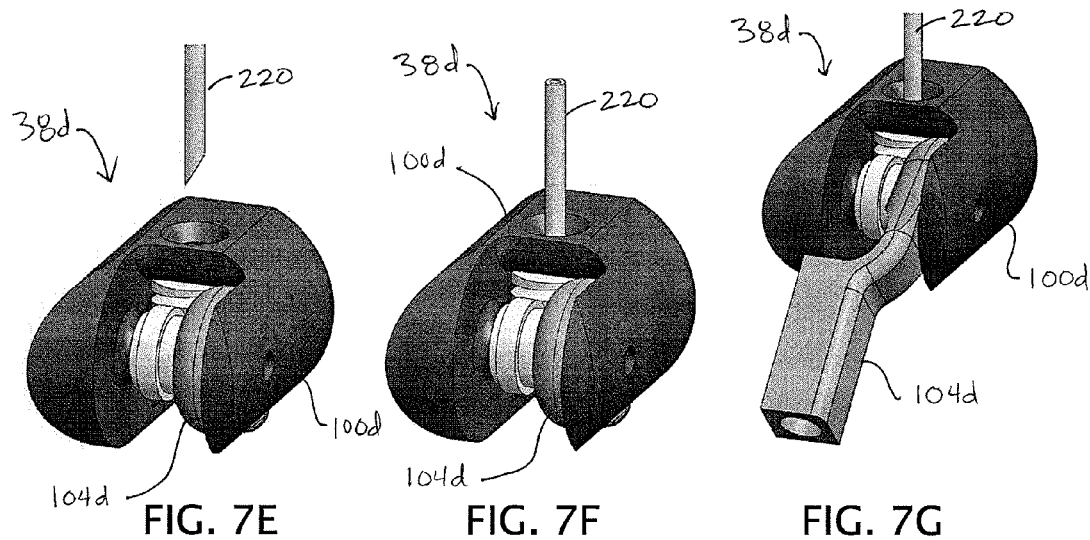

FIGS. 7A-7G depict various views of another embodiment 38d of the present medical devices, which can also be used as part of one of the present systems. Medical device 38d is similar in several respects to medical devices 38a, 38b, and 38c, so generally only the differences between them will be described here. In particular, medical device 38d is configured such that arm 104d can be rotated or deployed differently relative to platform 100d. In the embodiment shown, arm 104d is pivotally coupled to platform 100d such that arm 104d is rotatable at least 90 degrees around rotational axis 108 between a collapsed position (FIG. 7E) and an expanded position (FIG. 7G). In the embodiment shown, device 38d comprises: a first gear 212d coupled in fixed relation to arm 104d such that rotational axis 108 passes through first gear 212d (is substantially colinear with the rotational axis of first gear 212d); and a second gear 216d rotatably coupled to platform 100d. FIG. 7D is a partially cutaway view that omits a portion of platform 100d to show portions of device 38d in more detail.

Additionally, in the embodiment shown, device 38d is configured such that a tool 220 can be coupled to second gear 216d (e.g., as illustrated from FIG. 7D to FIG. 7E) such that tool 220 can be rotated to rotate second gear 216d; and such that if second gear 216d is rotated in a first rotational direction 224 when arm 104d is in the collapsed position (FIG. 7E), then arm will rotate from the collapsed position toward the expanded position (e.g., from FIG. 7E toward FIG. 7F). In the embodiment shown, device 38d is also configured such that: if second gear 216d is rotated in a second rotational direction 228 when arm 104d is in the expanded position (FIG. 7F), then arm 104d will rotate from the expanded position toward the collapsed position (e.g., from FIG. 7F toward FIG. 7E).

In the embodiment shown, second gear 216d is configured to rotate around a first gear axis 236d. In the embodiment shown, first gear axis 236d is substantially parallel to the rotational plane of arm 104d. In other embodiments, first gear axis 236d can be substantially perpendicular to the rotational plane of arm 104d. In the embodiment shown, first gear axis 236d is substantially perpendicular to the length of platform 100d (e.g., substantially perpendicular to the central longitudinal axis of arm 104d when arm 104d is in the collapsed position. In the embodiment shown, first gear 212d is unitary with arm 104d. In other embodiments, first gear 212d can be separately formed and held in fixed relation to arm 104d in any suitable fashion (e.g., with one or more pins or other fasteners, adhesive, welds, or the like). In the embodiment shown, second gear 216d comprises a worm gear coupled to platform 100d and first gear 212d such that second gear 216d can rotate relative to platform 100d and such that rotation of second gear 216d will cause rotation of first gear 212d (and thereby arm 104d). In the embodiment shown, platform 100d comprises an opening 240d (e.g., with a tapered top portion 244d) configured to permit tool 220 to be inserted into opening 240d and coupled to second gear 216d. For example, second gear 216d can comprise a hexagonal opening (e.g., configured to receive an Allen wrench), a hexagonal head (e.g., configured to be coupled to a socket wrench to cause second gear 216d to rotate, a female Phillips screw head (e.g., configured to be coupled to a Phillips screwdriver to cause second gear 216d to rotate), a flat-head screw head (e.g., configured to be coupled to a flat-head screwdriver to cause second gear 216d to rotate), a press-fit receiver, and/or any other suitable shape or structure to permit a tool 220 to be coupled to second gear 216d. As such, tool 220 can be any suitable tool configured to couple to second gear 216d, such as, for example, an Allen wrench, a socket wrench, a Phillips or flat-head screwdriver, a needle, a hook, and/or the like, as appropriate for various embodiments of the present devices.

Tool 220 can be inserted into the patient's body cavity transdermally and/or can be rotated by a motor once coupled to second gear 216d (e.g., a power tool). For example, as illustrated in FIGS. 7E-7G, a needle 220 can be inserted through opening 240 and coupled with second gear 216d by pressing the tip of needle 220 into second gear 216d (e.g., such that friction between needle 220 and second gear 216d permits needle 220 to rotate second gear 216d). Once needle 220 is inserted into and/or engages second gear 216d, needle 220 can be rotated to cause second gear 216d to rotate and deploy (rotate) arm 104d toward the expanded position shown in FIG. 7G. Needle 220 can be, for example, an 18-gauge hypodermic needle. Upon deployment or rotation of arm 104d to the desired angle relative to platform 100d, needle 220 can be removed from platform 100d and/or from the patient. In some embodiments, first and second gears 212d and 216d, respectively, are configured to have a relatively low efficiency for reversing the process (e.g., such that a greater torque is required to reverse the rotation of the arm (to return the arm to the collapsed position), such as, for example, so that the gears resist retraction of the arm to the collapsed position. In the embodiment shown, device 38d is configured to permit arm 104d to rotate and/or be substantially fixed at any angle between the collapsed position and the expanded position.

Figures 8A, 8B:
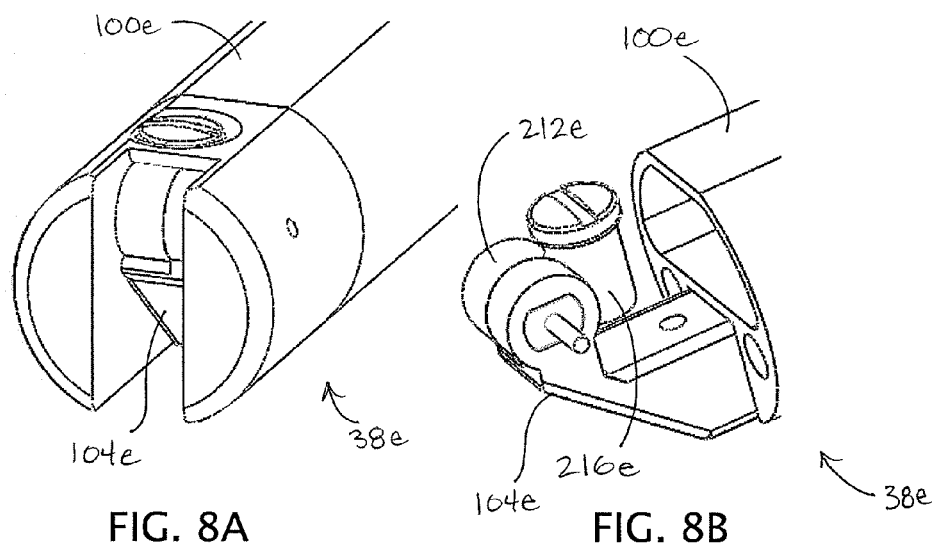
FIGS. 8A-8B depict various views of another embodiment of the present medical devices.

FIGS. 8A-8B depict various views of another embodiment 38e of the present medical devices, which can also be used as part of one of the present systems. Medical device 38e is similar in several respects to medical devices 38a, 38b, 38c, and 38d, so generally only the differences between them will be described here. In particular, medical device 38e is configured such that second gear 216e has a flat-head screw head such that second gear 216e can be coupled to and rotated by a flat-head screwdriver. Additionally, platform 100e and arm 104e are configured to fit closely together to minimize the possibility of body fluids and/or tissue infiltrating or contaminating first gear 212e and second gear 216e. For example, in the embodiment shown, second gear 216e is substantially enclosed. FIG. 8B is a partially cutaway view that omits a portion of platform 100e to show portions of device 38e in more detail.

Figure 9A:
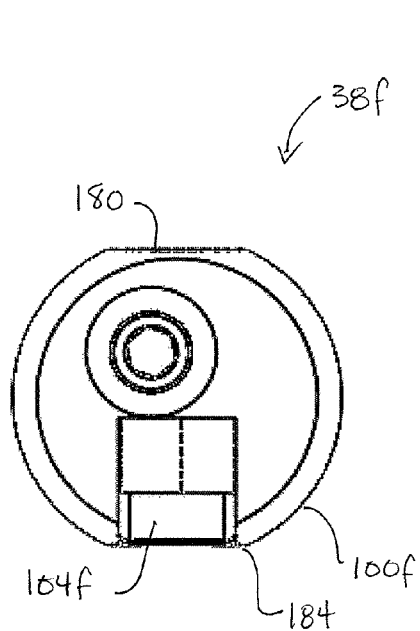
FIGS. 9A-9C depict various views of another embodiment of the present medical devices.
Figure 9B:
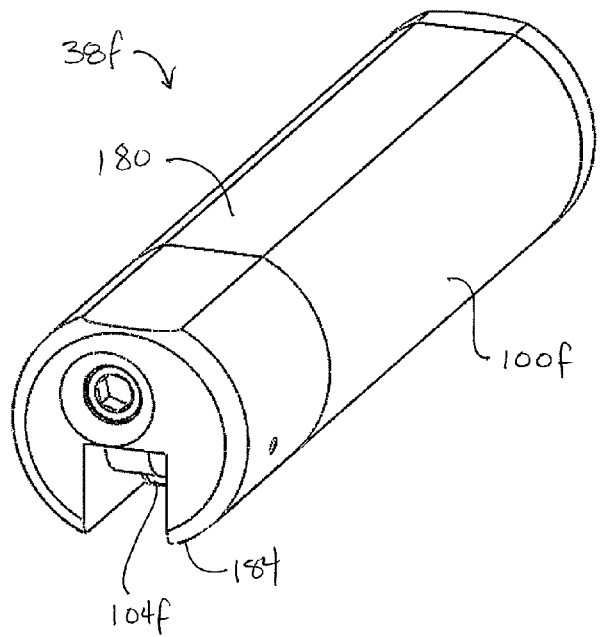
Figure 9C:
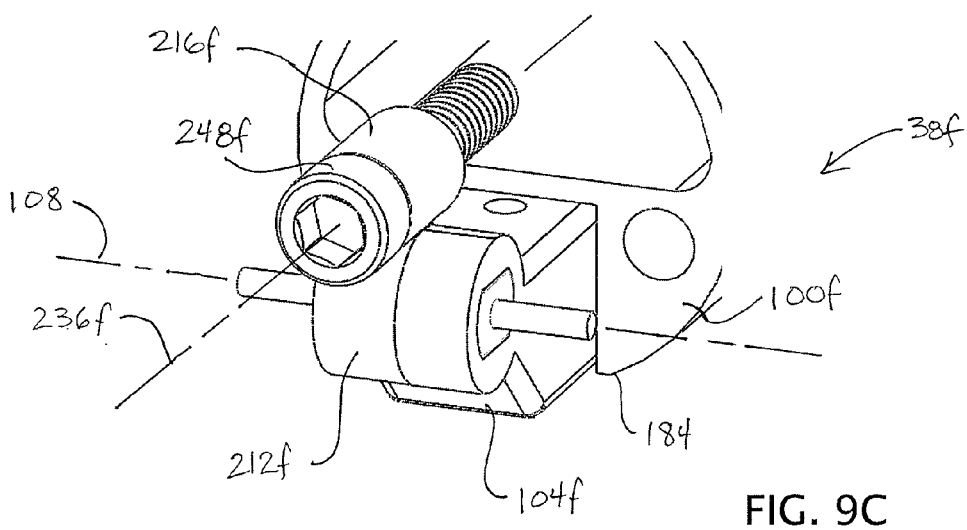

FIGS. 9A-9C depict various views of another embodiment 38f of the present medical devices, which can also be used as part of one of the present systems. Medical device 38f is similar in several respects to medical devices 38a, 38b, 38c, 38d, and 38e, so generally only the differences between them will be described here. In particular, medical device 38f is configured such that first gear axis 236f (rotational axis of second gear 216f) is substantially parallel to the length of platform 100f (e.g., substantially perpendicular to the central longitudinal axis of arm 104f when arm 104f is in the collapsed position). Additionally, in the embodiment shown, first gear axis 236f is closer to coupling side 180 of platform 100f than to working side 184, and rotational axis 108 is closer to working side 184 than coupling side 180. FIG. 9C is a partially cutaway view that omits a portion of platform 100f to show portions of device 38f in more detail. In the embodiment shown, second gear 216f is coupled to (e.g., threaded onto and/or secured with an adhesive, locknut, or the like) an Allen screw 248f such that rotation of screw 248f will rotate second gear 216f.

FIGS. 10A-10E depict various partially cutaway views of another embodiment 38g of the present medical devices, which can also be used as part of one of the present systems. In each of FIGS. 10A-10E, a large portion of platform 100g is omitted to show detent mechanism 116g and arm 104g in more detail. Medical device 38g is similar in several respects to medical devices 38a, 38b, 38c, 38d, 38e, and 38f, so generally only the differences between them will be described here. In particular, medical device 38g is configured such that first gear axis 236g is closer to working side 184 of platform 100g than to coupling side 180, and rotational axis 108 is closer to coupling side 180 than working side 184. Additionally, in the embodiment shown, second gear 216g is covered by housing 120g at distal end 124 of platform 100g such that an elongated member (not shown, but similar, for example, to a rod, threaded rod, bolt, or the like) can be coupled to second gear 216g and extended to proximal end 122 of platform 100g such that the elongated member can be coupled to a tool and/or rotated at proximal end 122 of platform 100g to cause second gear 216g and arm 104g to rotate.

Figures 11A, 11B:
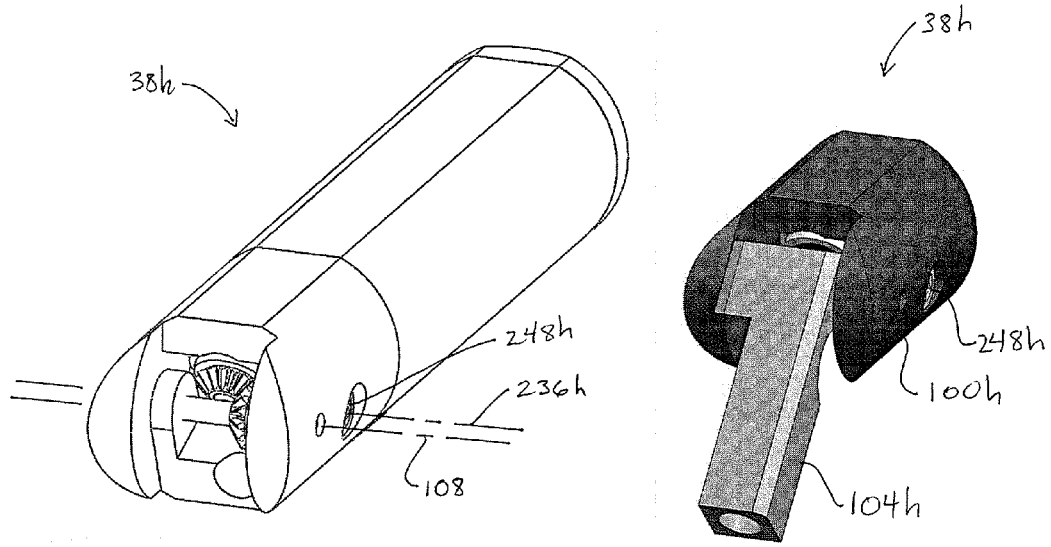
FIGS. 11A-11E depict various views of another embodiment of the present medical devices.
Figures 11C, 11D, 11E:
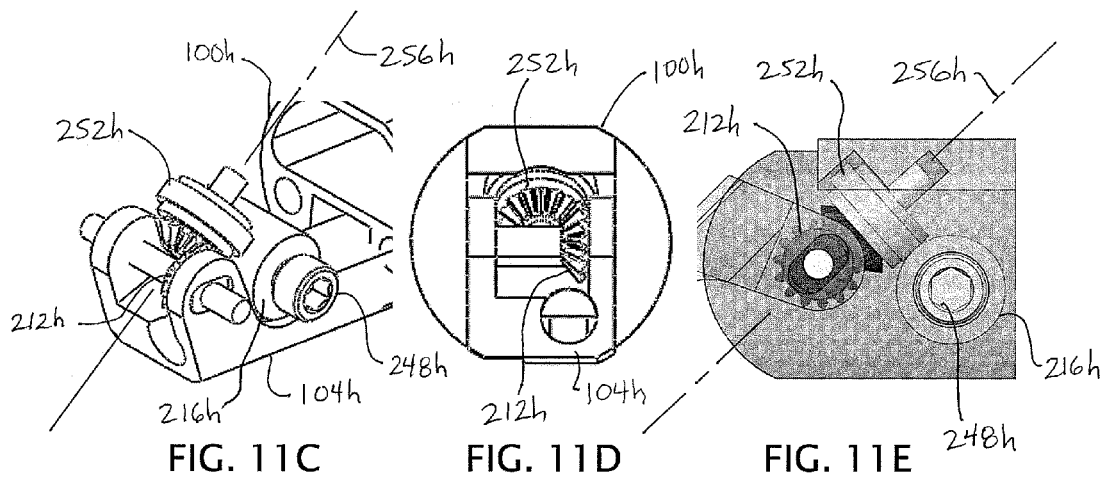

FIGS. 11A-11E depict various views of another embodiment 38h of the present medical devices, which can also be used as part of one of the present systems. Medical device 38h is similar in several respects to medical devices 38a, 38b, 38c, 38d, 38e, 38f, and 38g, so generally only the differences between them will be described here. In particular, medical device 38h is configured such that first gear axis 236h (and Allen screw 248h) is substantially perpendicular to the rotational plane of arm 104h. FIG. 11C is a partially cutaway view that omits a portion of platform 100h to show portions of device 38h in more detail. In the embodiment shown, medical device 38h further comprises: a third gear 252h coupled to first gear 212h and second gear 216h such that if second gear 216h is rotated, second gear 216h will rotate third gear 252h and third gear 252h will rotate first gear 212h. In the embodiment shown, third gear 252h is configured to rotate around a second gear axis 256h that is substantially perpendicular to first gear axis 236h. In the embodiment shown, first gear 212h comprises a bevel gear coupled in fixed relation to arm 104h, third gear 252h comprises a worm-gear follower with a bevel gear rotatably coupled to platform 100h and configured to engage and rotate with first gear 212h, and second gear 216h comprises a worm gear rotatably coupled to platform 100h and configured to engage and rotate with third gear 252h.

Figure 12A:
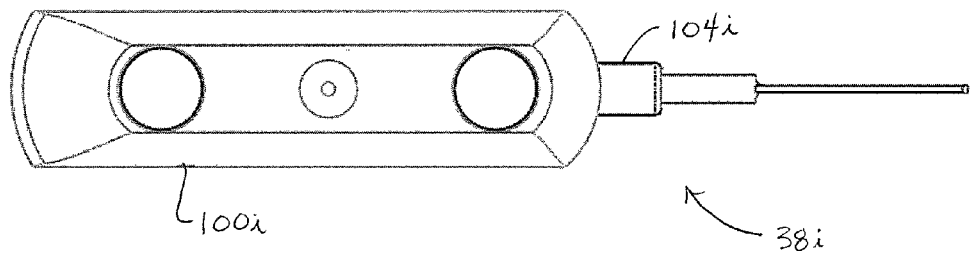
FIGS. 12A-12C depict various views of another embodiment of the present medical devices.
Figure 12B:
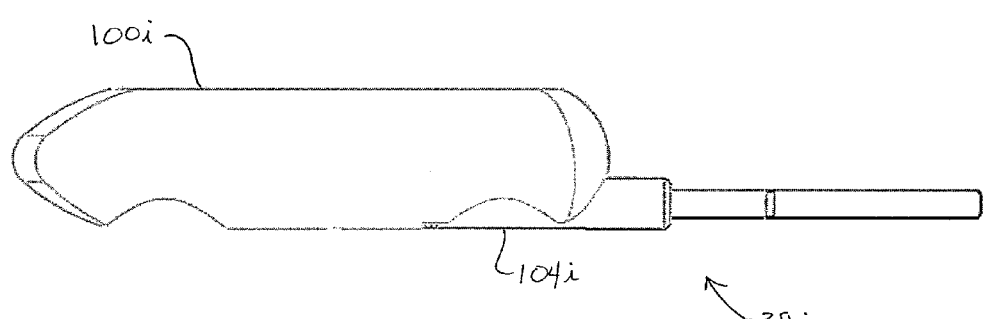
Figure 12C:
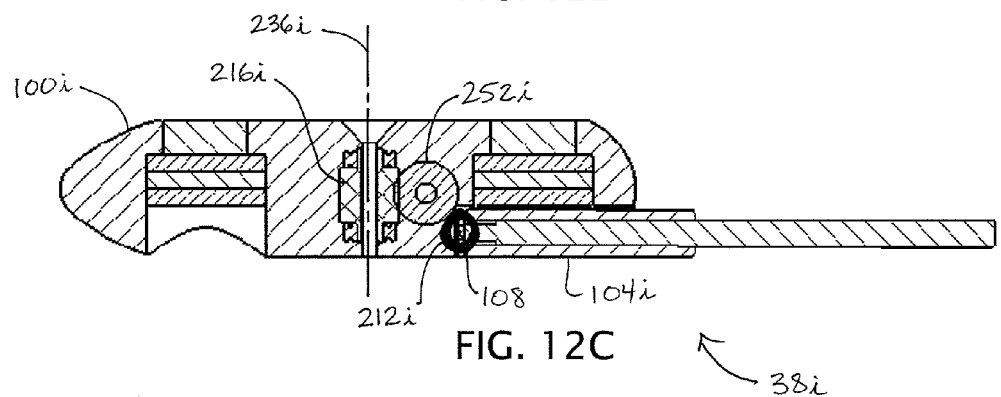

FIGS. 12A-12C depict various views of another embodiment 38i of the present medical devices, which can also be used as part of one of the present systems. Medical device 38i is similar in several respects to medical devices 38a, 38b, 38c, 38d, 38e, 38f, 38g, and 38h, so generally only the differences between them will be described here. In particular, medical device 38i is configured such that arm 104i is rotatable around rotational axis 108 by less than 90 degrees (e.g., such that expanded position is where arm 104i is rotated between 30 and 60 degrees clockwise from the collapsed position shown in FIGS. 12B and 12C). In the embodiment shown, second gear 212i is rotatably coupled to platform 100i such that first gear axis 236i is substantially perpendicular to rotational axis 108 of arm 104i and such that first gear axis 236i is substantially parallel to the rotational plane of arm 104i. In the embodiment shown, first gear axis 236i is also substantially perpendicular to the length of platform 100i (e.g., substantially perpendicular to the central longitudinal axis of arm 104i when arm 104i is in the collapsed position.

Figure 13A:
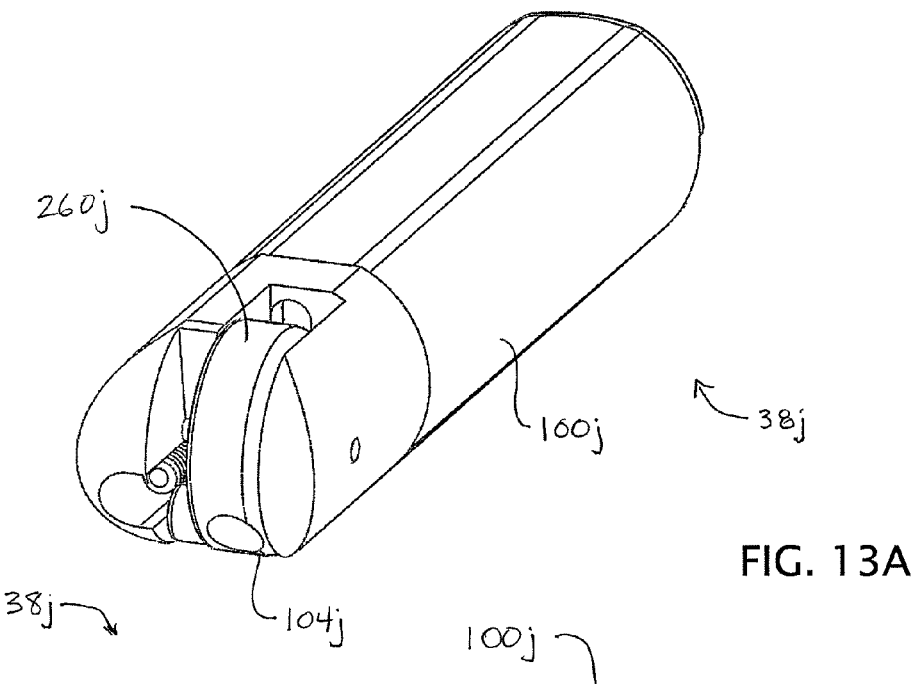
FIGS. 13A-13I depict various views of another embodiment of the present medical devices.
Figure 13B:
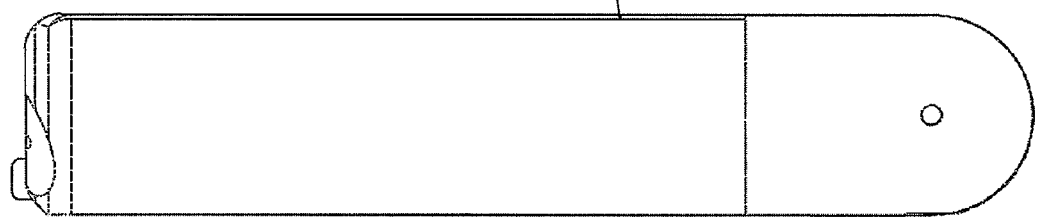
Figure 13C:
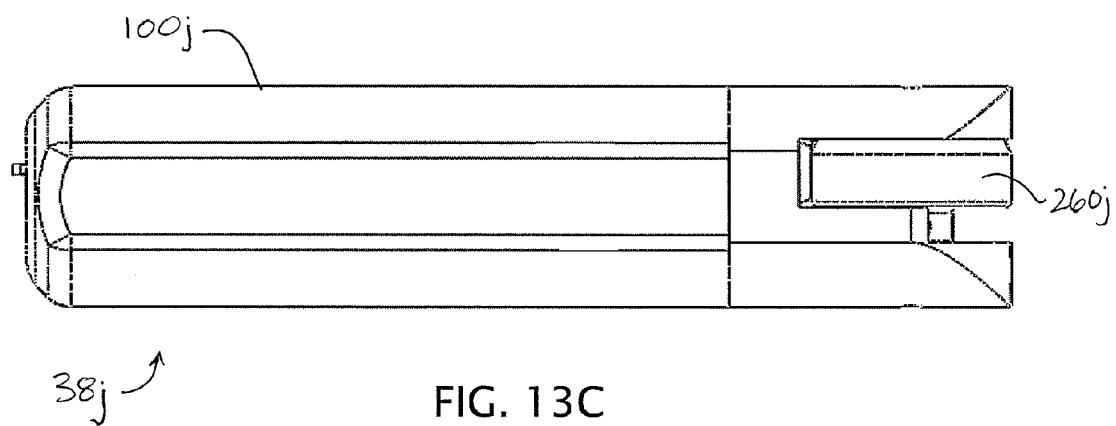
Figure 13D:
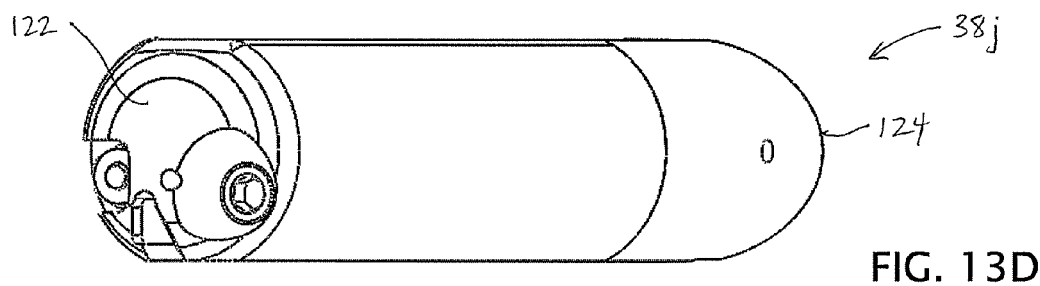
Figure 13E:
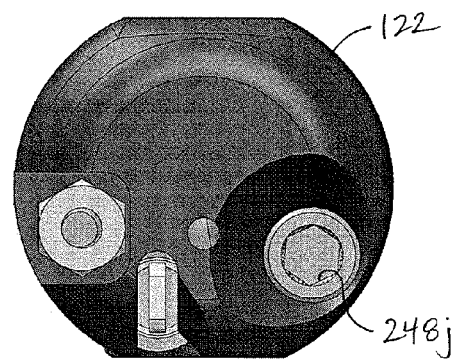
Figure 13F:
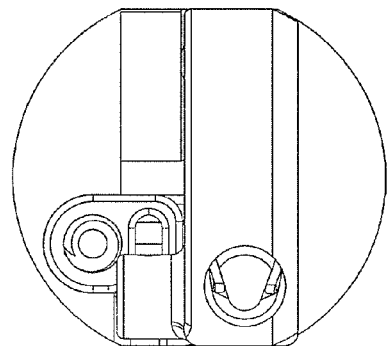
Figure 13G:
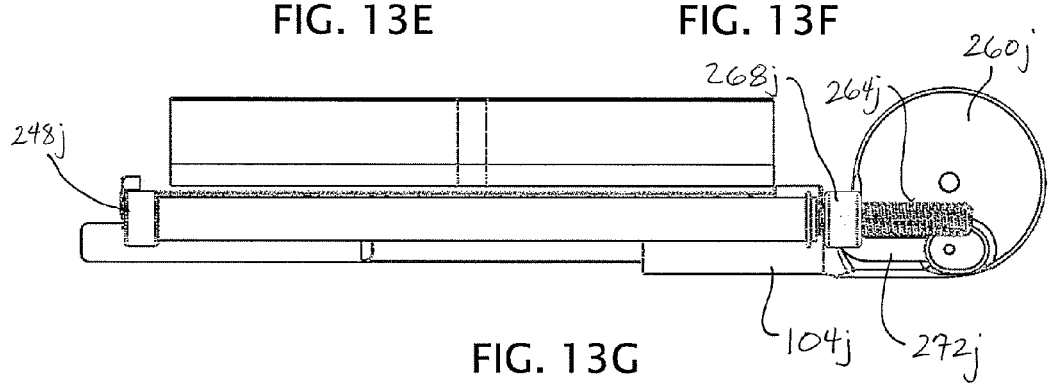
Figure 13H:
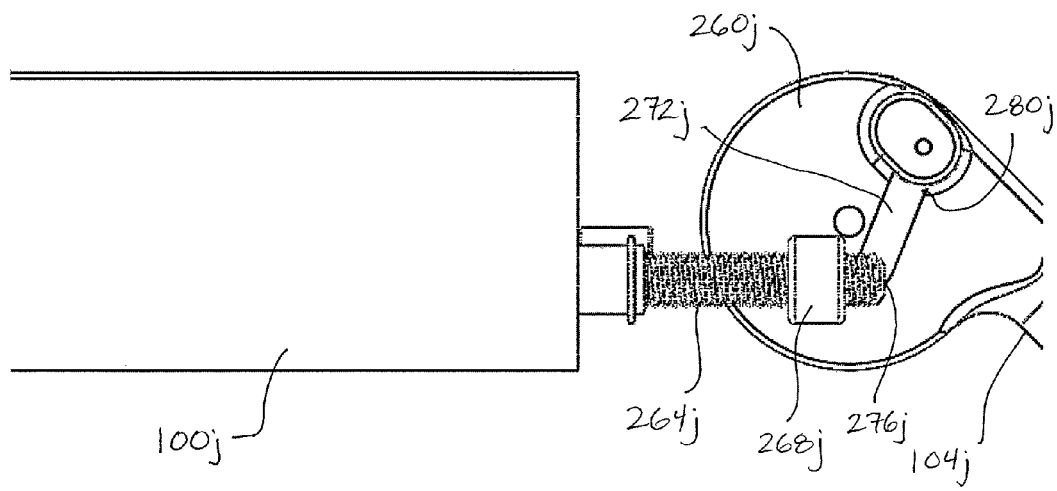
Figure 13I:
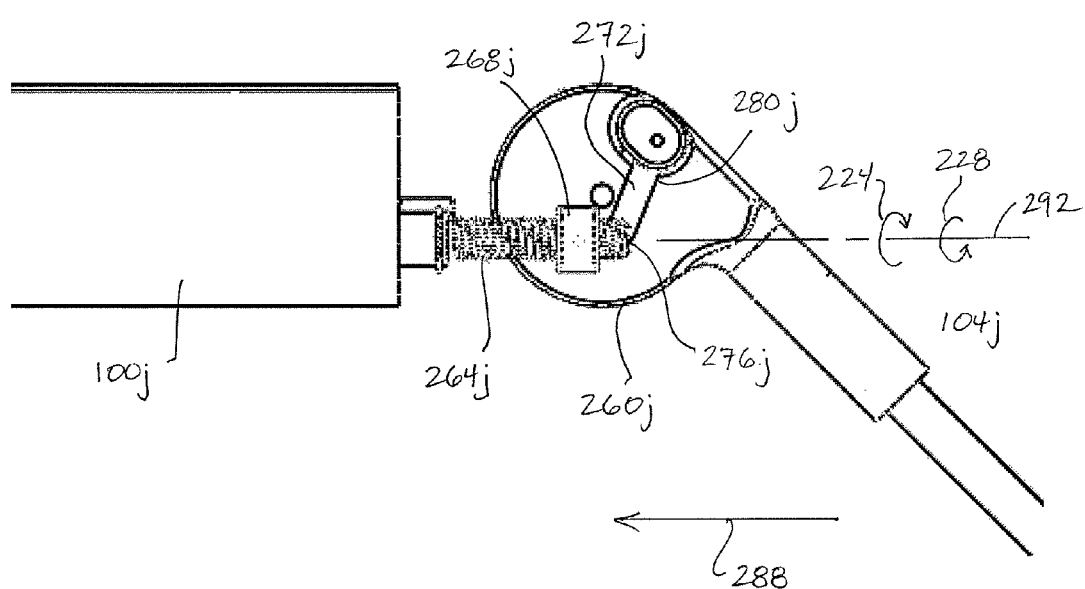

FIGS. 13A-13I depict various views of another embodiment 38j of the present medical devices, which can also be used as part of one of the present systems. Medical device 38j is similar in several respects to medical devices 38a, 38b, 38c, 38d, 38e, 38f, 38g, 38h, and 38i, so generally only the differences between them will be described here. In particular, medical device 38j is configured such that arm 104j can be adjusted and secured relative to platform 100j in a different fashion. In the embodiment shown, arm 104j has a hub 260j that is pivotally coupled to platform 100j such that arm 104j is rotatable at least 90 degrees around rotational axis 108 between a collapsed position (FIG. 13H) and an expanded position (FIG. 13I). FIG. 13G is a cutaway view in which platform 100j is omitted to show the other parts of device 38j in more detail, and FIGS. 13H and 13I are partially cutaway views that omits a portion of platform 100j to show portions of device 38j in more detail.

In the embodiment shown, medical device 38j also comprises: a threaded member 264j rotatably coupled to platform 100j; a shuttle 268j coupled to threaded member 264j; and a shuttle arm 272j having a first end 276j coupled (e.g., pivotally coupled) to shuttle 268j and a second end 280j coupled (e.g., pivotally coupled) to hub 260j. In the embodiment shown, medical device 38j is configured such that: a tool (e.g., 220) can be coupled to threaded member 264j such that the tool can be rotated to rotate threaded member 264j; and if threaded member 264j is rotated in a first rotational direction 224 when the arm is in the collapsed position, then shuttle 268j will travel in a substantially linear first direction 284 to cause arm 104j to rotate from the collapsed position toward the expanded position. In the embodiment shown, medical device 38j is also configured such that: if threaded member 264j is rotated in a second rotational direction 228 when arm 104j is in the expanded position, then shuttle 268j will travel in a substantially linear second direction 288 (that is substantially opposite first direction 284) to cause arm 104j to rotate from the expanded position toward the collapsed position. Threaded member 264j can be entirely threaded, or can have only a portion (e.g., a portion sufficient to permit the shuttle to travel between the collapsed and expanded positions of the arm). In the embodiment shown, threaded member 264j is configured to be coupled to a tool (e.g., such that tool can rotate threaded member 264j) at or near proximal end 122 of platform 100j (e.g., via Allen screw head 248j). Threaded member 264j is configured to rotate around a member axis 292 that is substantially parallel to the rotational plane of arm 104j.

Figure 14A:
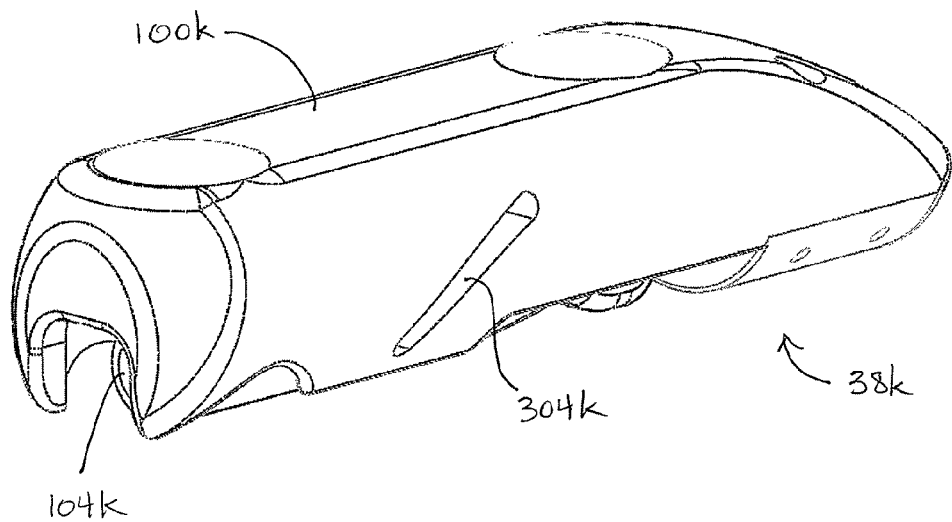
FIGS. 14A-14D depict various views of another embodiment of the present medical devices.
Figure 14B:
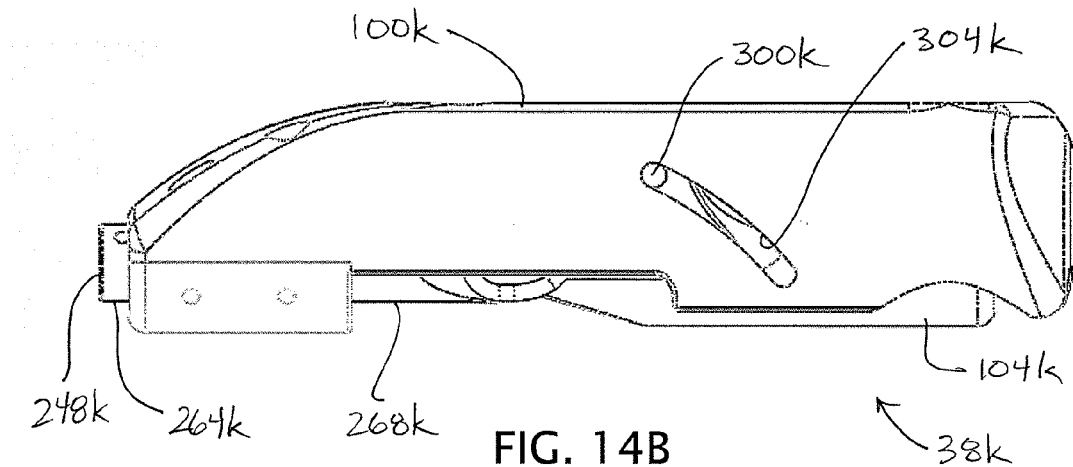
Figure 14C:
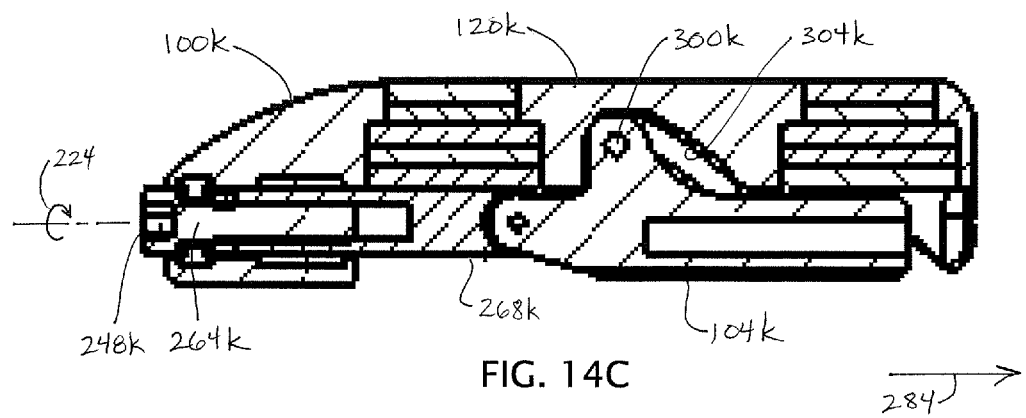
Figure 14D:
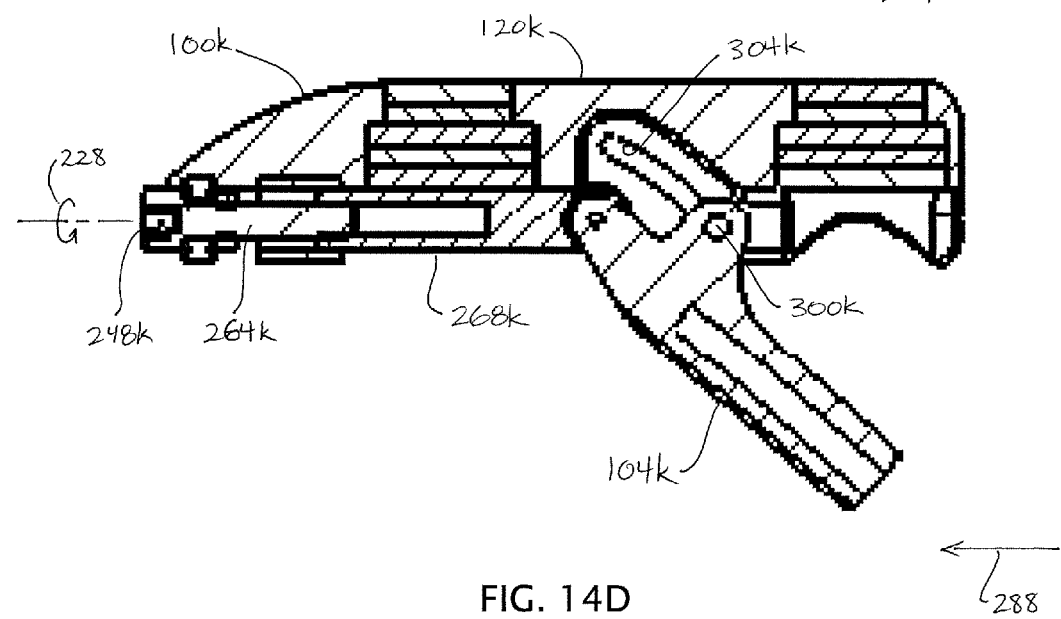

FIGS. 14A-14D depict various views of another embodiment 38k of the present medical devices, which can also be used as part of one of the present systems. Medical device 38k is similar in several respects to medical devices 38a, 38b, 38c, 38d, 38e, 38f, 38g, 38h, 38i, and 38j, so generally only the differences between them will be described here. In particular, medical device 38k is configured such that arm 104k is coupled to platform 100k by way of slots and pins. In the embodiment shown, arm 104k is coupled to platform 100k with a pin 300k slidably disposed within a cam slot 304k defined within one of platform 100k and arm 104k, where the pin is coupled to the other of the platform and the arm, and the arm movable between an expanded position (FIG. 14D) and a collapsed position (FIG. 14C).

As with device 38j, medical device 38k includes a threaded member 264k rotatably coupled to platform 100k; a shuttle 268k coupled to threaded member 264k. In the embodiment shown, shuttle 268k is pivotally coupled to arm 104k. Medical device 38k is configured such that: a tool (e.g., 200) can be coupled to threaded member 264k such that the tool can be rotated to rotate threaded member 268k; and if threaded member 268k is rotated in a first rotational direction 224 when arm 104k is in the collapsed position, then shuttle 268k will travel in a substantially linear first direction 284 to cause arm 104k to move from the collapsed position toward the expanded position.

For example, in the embodiment shown, cam slot 304k is formed in housing 120k of platform 100k, and pin 300k is coupled in fixed relation to arm 104k such that pin 300k is slideably received in cam slot 304k. More particularly, housing 120k of platform 100k includes one or more cam slots 304k (two, in the depicted embodiment) that are angularly disposed relative to the longitudinal axis of platform 100k and that extend transversely through at least a portion of the platform. In some embodiments, platform 100k can include a second cam slot (not shown, but parallel to substantially linear directions 284, 288) extending transversely through at least a portion of the platform. In the embodiment shown, proximal end 164 of arm 100k is coupled to platform 100k by pin or pins 300k extending into cam slots 304k, such that in moving from the collapsed position of FIG. 14C to the expanded position of FIG. 14D, arm 104k moves both longitudinally with shuttle 268k in the direction of distal end 124 of platform 100k and angularly outward from platform 100k. In the embodiment shown, threaded member 264k includes an Allen screw head 248k to receive a tool that comprises an Allen wrench.

Figure 15A:
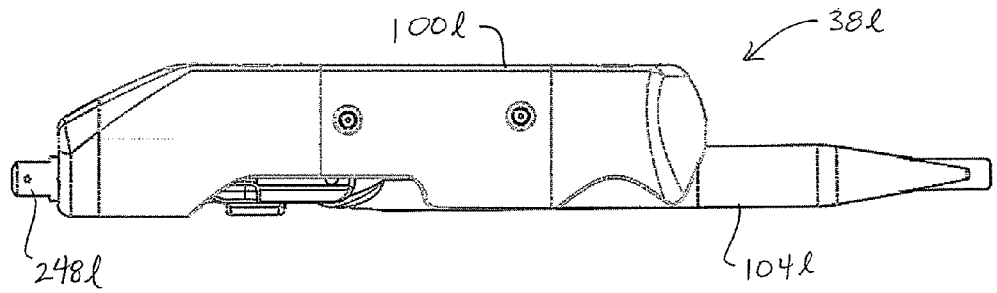
FIGS. 15A-15C depict various views of another embodiment of the present medical devices.
Figure 15B:
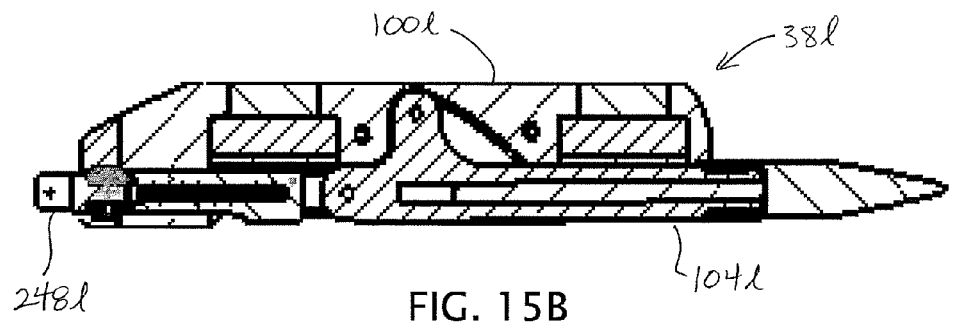
Figure 15C:
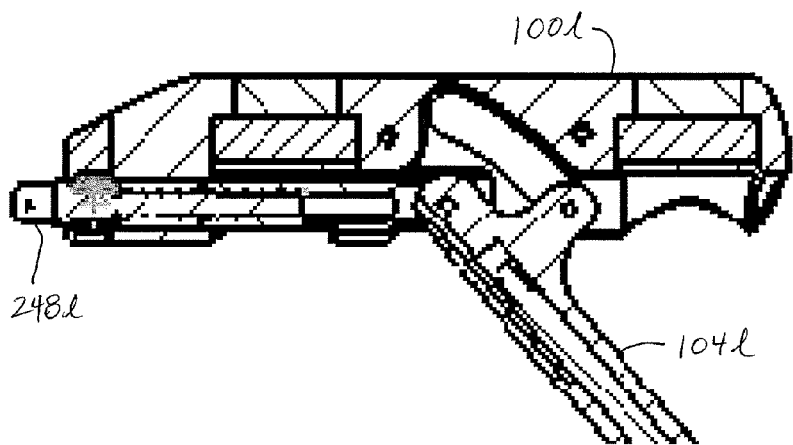

FIGS. 15A-15C depict various views of another embodiment 38l of the present medical devices, which can also be used as part of one of the present systems. Medical device 38l is similar in several respects to medical devices 38a, 38b, 38c, 38d, 38e, 38f, 38g, 38h, 38i, 38j, and 38k, so generally only the differences between them will be described here. In particular, threaded member 264l comprises a tab 248l with a hole configured to receive a tool (e.g., 220) that includes a hook to rotate threaded member 264l.

Figure 16A:
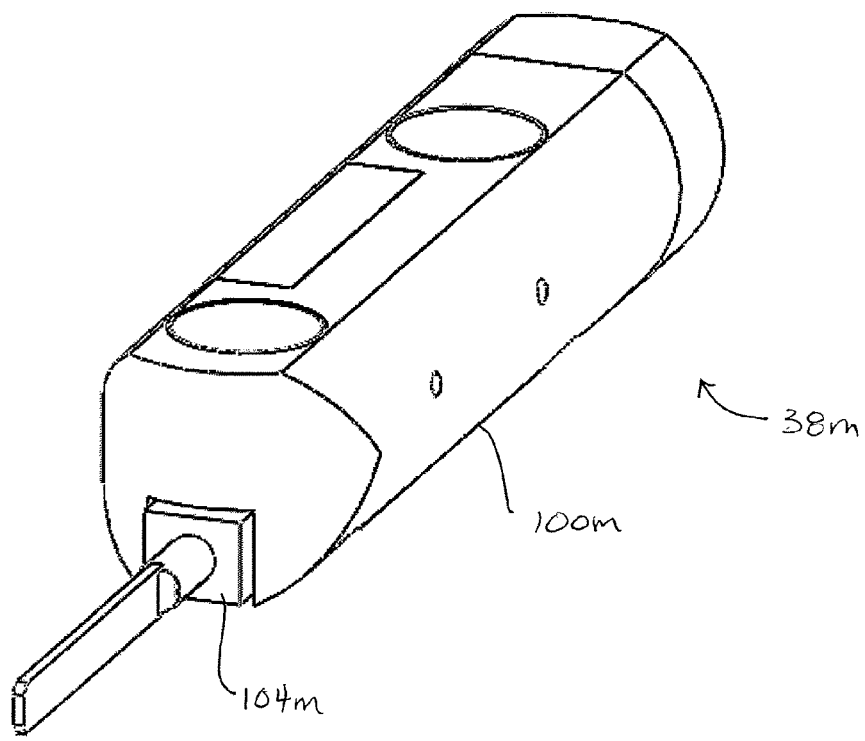
FIGS. 16A-16B depict various views of another embodiment of the present medical devices.
Figure 16B:
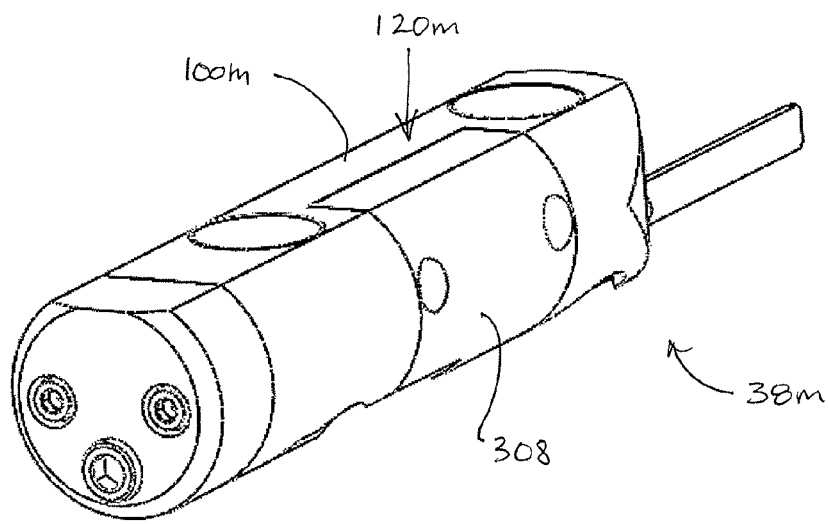

FIGS. 16A-16B depict various views of another embodiment 38m of the present medical devices, which can also be used as part of one of the present systems. Medical device 38m is similar in several respects to medical devices 38a, 38b, 38c, 38d, 38e, 38f, 38g, 38h, 38i, 38j, 38k, and 38l, so generally only the differences between them will be described here. In particular, medical device 38m is substantially similar to device 38l, but is configured such that housing 120m of platform 100m includes a side access panel 308 that can be removed to access internal components of device 38m. As illustrated for device 38m, the arm (e.g., 104m) of the present devices (e.g., 38m) can be can have a rectangular cross section and/or longitudinal recess 132 can be provided with a cross-sectional shape that matches the cross-sectional shape of the arm (e.g., to reduce the likelihood of debris from entering longitudinal recess 132 while the arm is in the collapsed position).

Figure 17A:
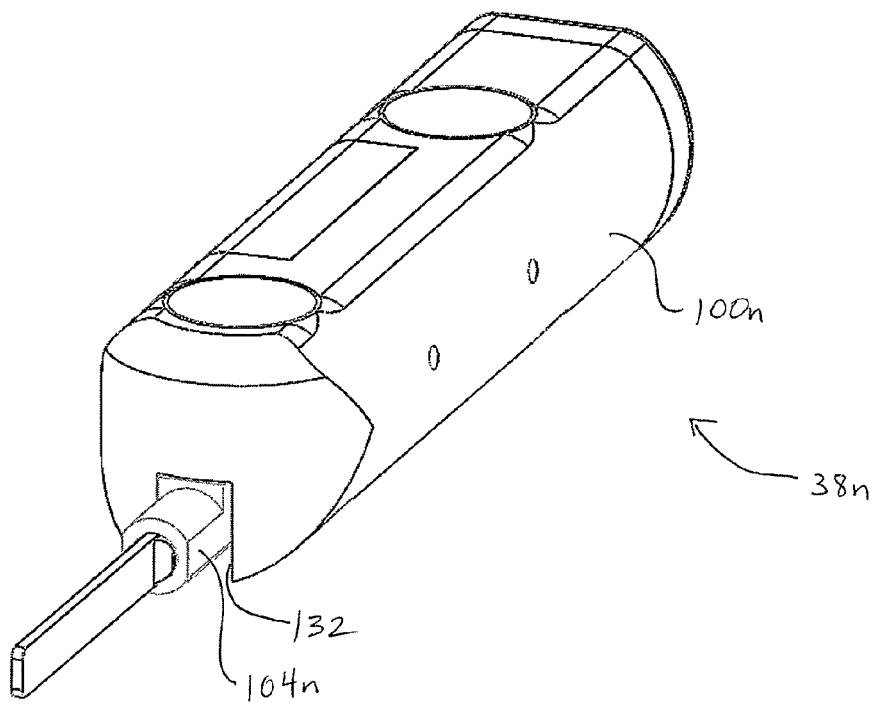
FIGS. 17A-17B depict various views of another embodiment of the present medical devices.
Figure 17B:
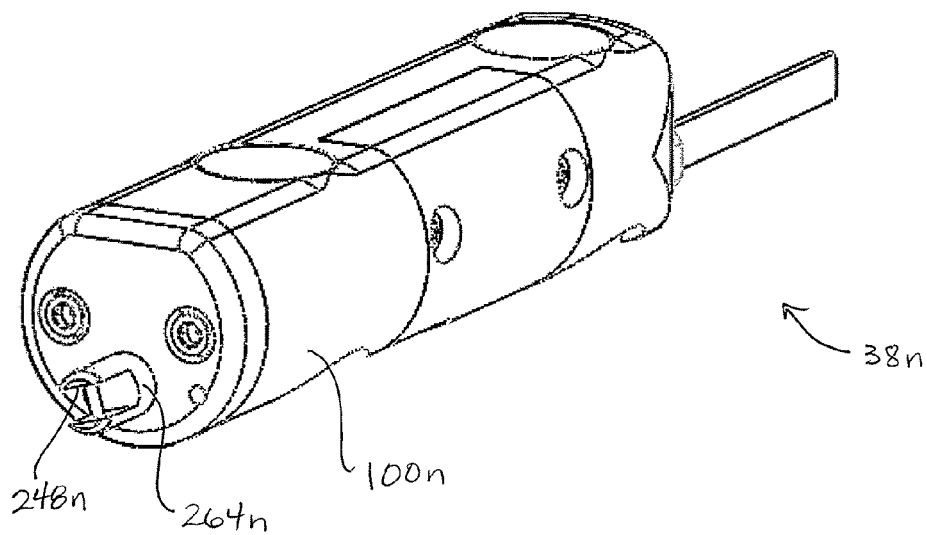
Figure 18A:
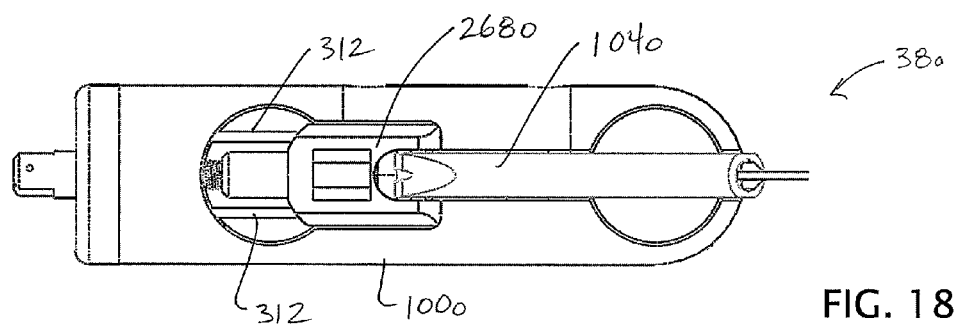
Figures 18B, 18C:
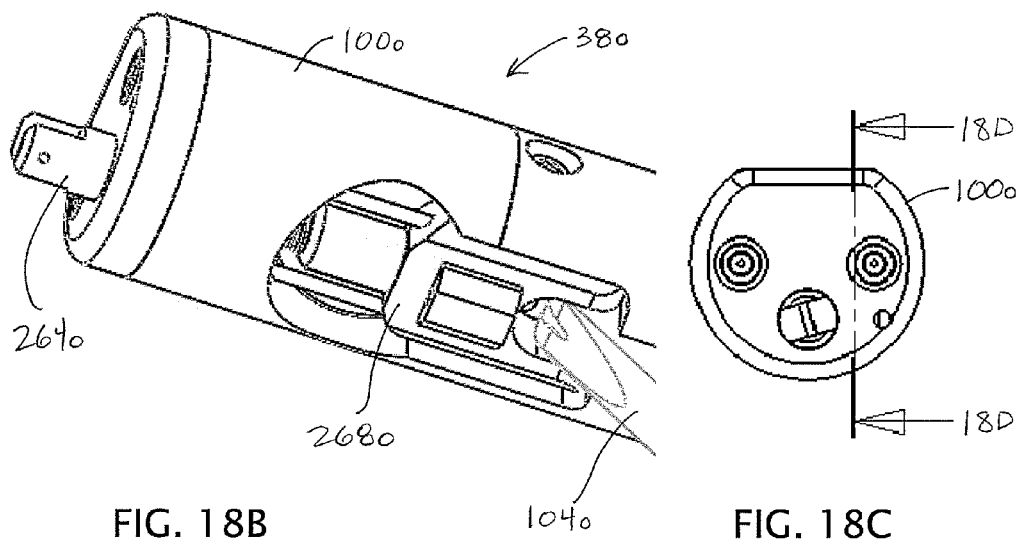
Figure 18D:
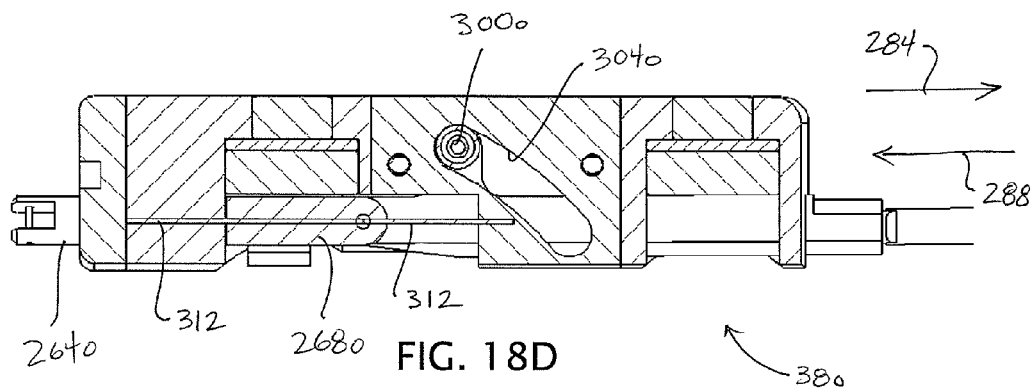
Figures 18I, 18J:
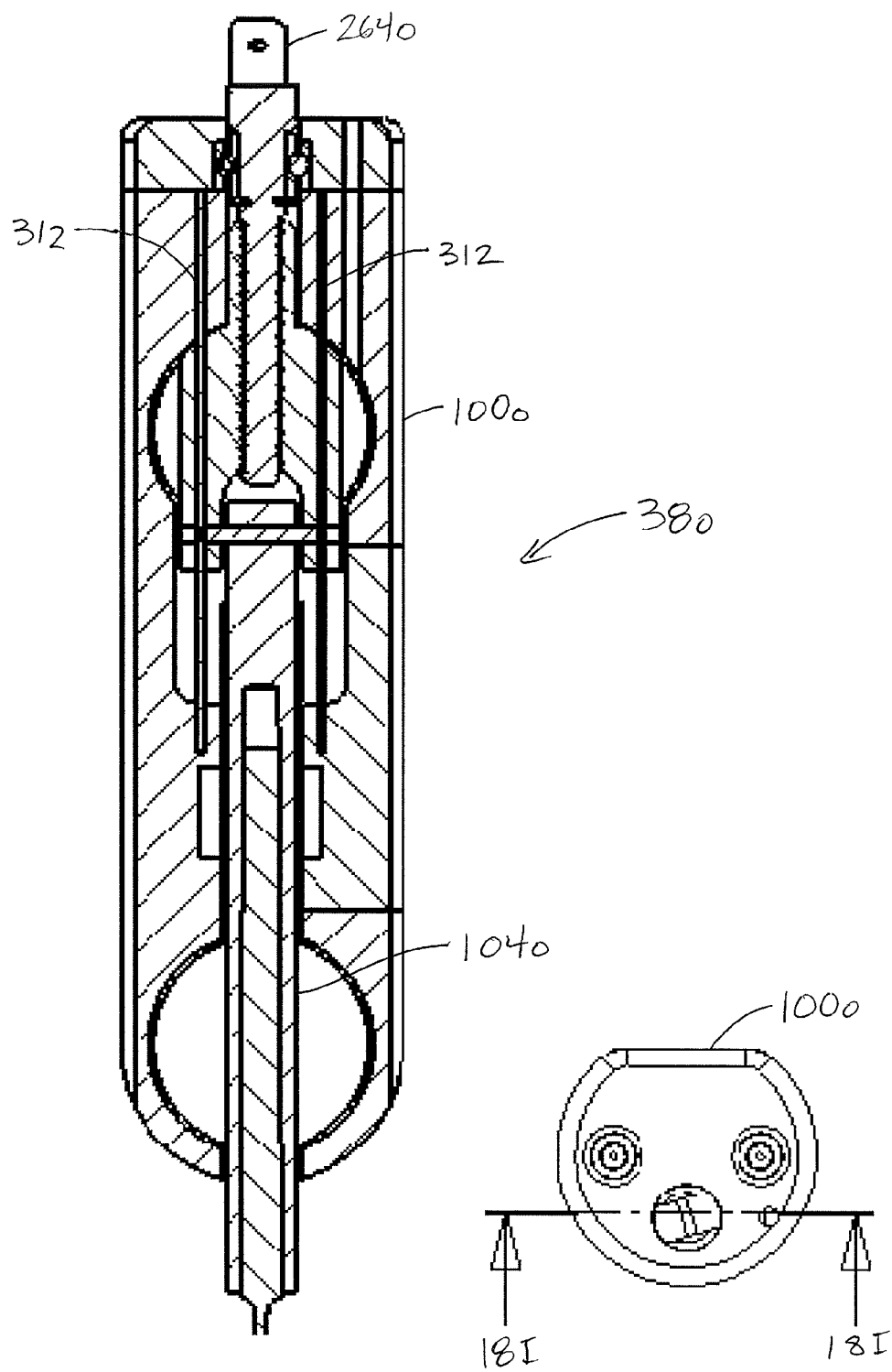
Figures 20A, 20B:
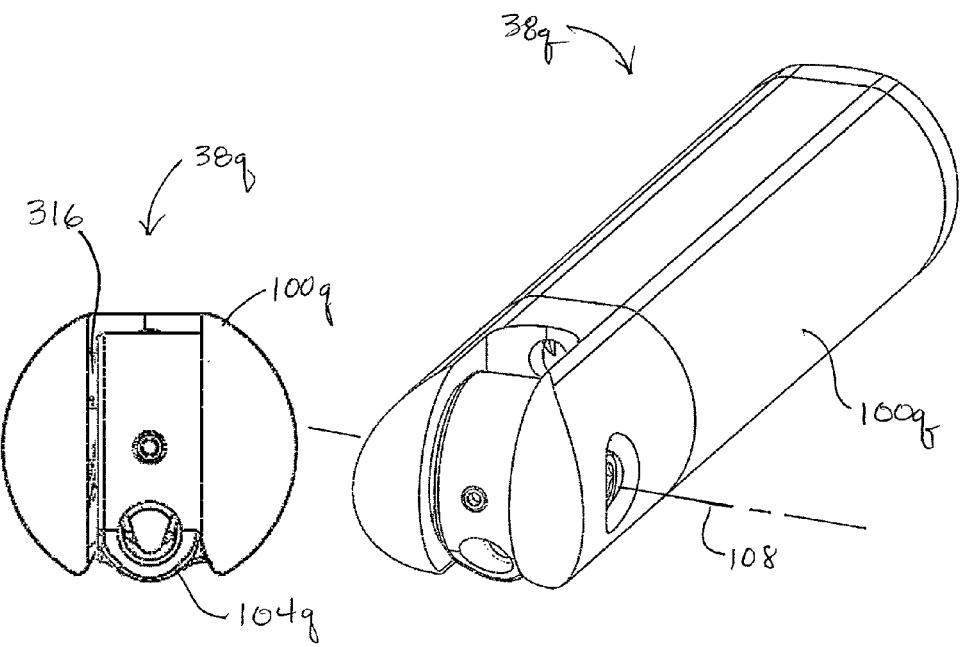
FIGS. 20A-20F depict various views of another embodiment of the present medical devices.
Figure 20C:
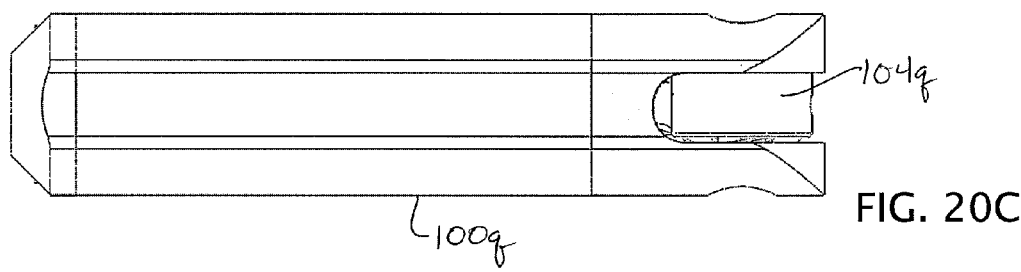
Figure 20D:
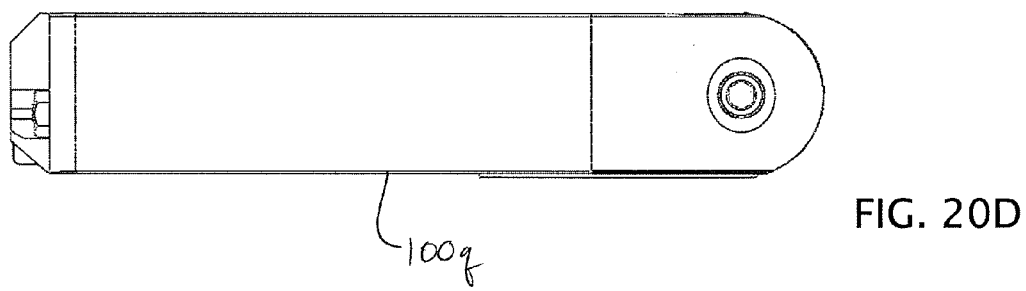
Figure 20E:
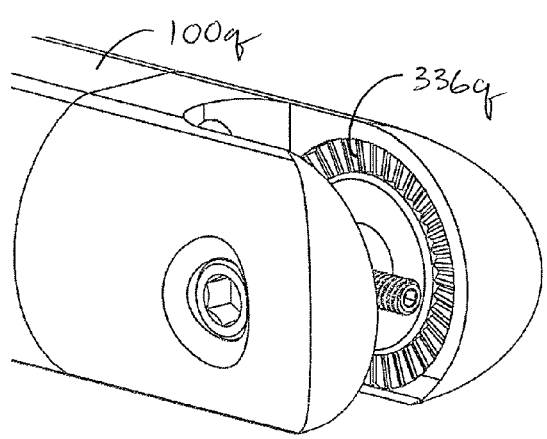
Figure 20F:
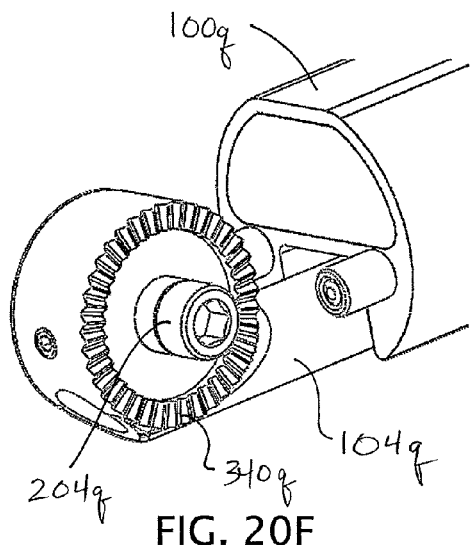

FIGS. 17A-17B depict various views of another embodiment 38n of the present medical devices, which can also be used as part of one of the present systems. Medical device 38n is similar in several respects to medical devices 38a, 38b, 38c, 38d, 38e, 38f, 38g, 38h, 38i, 38j, 38k, 38l, and 38m, so generally only the differences between them will be described here. In particular, medical device 38n is substantially similar to device 38l, but is configured such that threaded member 264*n* includes a slotted end 248*n* with a post across the slot such that the slot can receive a tool (e.g., 220) that includes a hook to rotate threaded member 264*n*.

FIGS. 18A-18J depict various views of another embodiment 38*o* of the present medical devices, which can also be used as part of one of the present systems. Medical device 38*o* is similar in several respects to medical devices 38*a*, 38*b*, 38*c*, 38*d*, 38*e*, 38*f*, 38*g*, 38*h*, 38*i*, 38*j*, 38*k*, 38*l*, 38*m*, and 38*n*, so generally only the differences between them will be described here. In particular, medical device 38*o* is substantially similar to device 38*l*, but is configured such that platform 100*o* includes one or more (e.g., two, as shown) guide rods 312 that are substantially parallel to the longitudinal axis of platform 100*o*. In the embodiment shown, shuttle 268*o* is slidably coupled to guide rods 312. Additionally, in the embodiment shown, medical device 38*o* is configured such that: if threaded member 264*o* is rotated in a first rotational direction 224 when arm 104*o* is in the collapsed position, then shuttle 268*o* will travel in a substantially linear first direction 284 along guide rods 312 to cause arm 104*o* to move from the collapsed position toward the expanded position. In this configuration, guide rods 312 are configured to act as linear bearings by helping to constrain or limit shuttle 268*o* to forward/back linear motion along guide rods 312.

FIGS. 19A-19K depict various views of another embodiment 38*p* of the present medical devices, which can also be used as part of one of the present systems. Medical device 38*p* is similar in several respects to medical devices 38*a*, 38*b*, 38*c*, 38*d*, 38*e*, 38*f*, 38*g*, 38*h*, 38*i*, 38*j*, 38*k*, 38*l*, 38*m*, 38*n*, and 38*o*, so generally only the differences between them will be described here. In particular, arm 104*p* is pivotally coupled to platform 100*p* such that arm 104*p* is rotatable around rotational axis 108 between a collapsed position (FIG. 19H) and an expanded position (FIG. 19K). Medical device 38*p* comprises: a spring 316 configured to bias arm 104*p* toward platform 100*p* in a first direction 320 that substantially parallel to rotational axis 108. In the embodiment shown, medical device 38*p* is configured such that: in the absence of an external force arm 104*p* can contact platform 100*p* such that arm 104*p* is substantially prevented from rotating relative to platform 100*p*; a tool (e.g., 220) can be coupled to arm 104*p* to move arm 104*p* relative to platform 100*p* in a second direction 324 that is substantially parallel to rotational axis 108; and if arm 104*p* is moved in second direction 324 such that arm 104*p* is separated from platform 100*p* then arm 104*p* is permitted to rotate relative to platform 100*p*. FIG. 19E is a partially cutaway view that omits a portion of platform 100*p* to show portions of device 38*p* in more detail, FIG. 19F is a cutaway view showing only the portion of platform 100*p* that includes tongue 328, and FIG. 19G is a cutaway view showing only the portion of arm 104*p* that includes grooves 332.

In the embodiment shown, one of platform 100*p* and arm 104*p* (platform 100*p* in the embodiment shown) comprises a tongue 328, the other of platform 100*p* and arm 104*p* (arm 104*p* in the embodiment shown) comprises a groove 332, and device 38*p* is configured such that if tongue 328 is aligned with groove 332 and arm 104*p* contacts platform 100*p*, then tongue 328 and groove 332 cooperate to substantially prevent rotation of the arm relative to the platform. In the embodiment shown, arm 104*p* comprises two grooves 332 that intersect each other and rotational axis 108 (e.g., two grooves 332 whose respective central axes intersect). In the embodiment shown, grooves 332 are disposed at an angle 334 of between 30 and 60 degrees (e.g., equal to, greater than, or between any of: 30, 35, 40, 45, 50, 55, and/or 60 degrees) relative to one another. For example, in the embodiment shown, one of the two grooves 332 corresponds to the collapsed position of the arm, and the other of the two grooved 332 corresponds to the expanded position of the arm.

FIGS. 19H-19K illustrate the deployment or rotation of arm 104*p* (the groove and tongue are on the opposite side of the arm in FIGS. 19H-19K, for clarity in the illustrated perspective, but the function and construction are otherwise substantially similar). More particularly, in the embodiment shown, an axle 204*p* is coupled in fixed relation to arm 104*p* and axle 204*p* includes a slotted end with a post across the slot such that the slot can receive a tool (e.g., 220) that includes a hook to engage the post of axle 204*p* in the slot of axle 204*p*. As shown in FIG. 19H tool engages axle 204*p* such that tool can pull axle 204*p* and arm 104*p* in first direction 320 to compress spring 316 and separate arm 104*p* (and groove 332) from platform 100*p* (and tongue 328). Upon separation of arm 104*p* from platform 100*p* (e.g., by at least the greater of the height of tongue 328 or the depth groove 332), as shown in FIG. 19F, then arm 104*p* is permitted to rotate relative to platform 100*p*, as shown in FIG. 19G. When or while arm is rotated from the collapsed position to the expanded position, arm 104*p* can be permitted to return to its biased state in which arm 104*p* is in contact with platform 100*p*, such that when tongue 328 is aligned with the groove 332 that corresponds to the expanded position of arm 104*p*, arm 104*p* will be substantially prevented from rotating relative to platform 100*p*.

FIGS. 20A-20F depict various views of another embodiment 38*q* of the present medical devices, which can also be used as part of one of the present systems. Medical device 38*q* is similar in several respects to medical devices 38*a*, 38*b*, 38*c*, 38*d*, 38*e*, 38*f*, 38*g*, 38*h*, 38*i*, 38*j*, 38*k*, 38*l*, 38*m*, 38*n*, 38*o*, and 38*p*, so generally only the differences between them will be described here. In particular, medical device 38*q* is substantially similar to device 38*p*, but platform 100*q* comprises a first set of teeth 336; arm 104*q* comprises a second set of teeth 340, and medical device 38*q* is configured such that: in the absence of an external force, first set of teeth 336 contacts second set of teeth 340 such that arm 104*p* is substantially prevented from rotating relative to platform 100*p*; and a tool can be coupled to medical device 38*q* (e.g., to axle 204*q*) to rotate arm 104*q* around rotational axis 108. For example, in the embodiment shown, axle 204*q* comprises an Allen screw configuration, and due to the angled surfaces and relatively shallow depth of the teeth, arm 104*q* can be rotated relative to platform 100*q* without first pulling arm 104*q* away from platform 100*q* (e.g., the angled surfaces of the teeth can be configured such that the lateral component of a torque applied to axle 204*q* is sufficient to separate arm 104*q* and platform 100*q* to permit rotation of the arm). In other embodiments, arm 104*q* can be pulled or otherwise separated from platform 100*q* before rotating arm 104*q* relative to platform 100*q*.

Figure 21A:
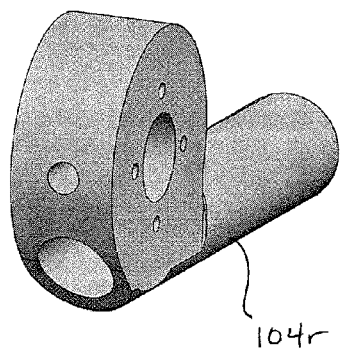
FIGS. 21A-21B depict various views of an arm suitable for use with the medical device of FIGS. 20A-20F.
Figure 21B:
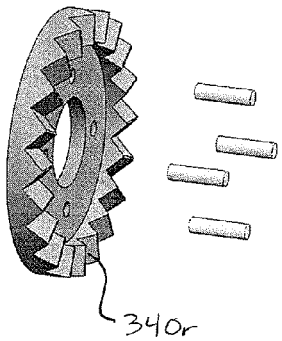
Figure 22E:
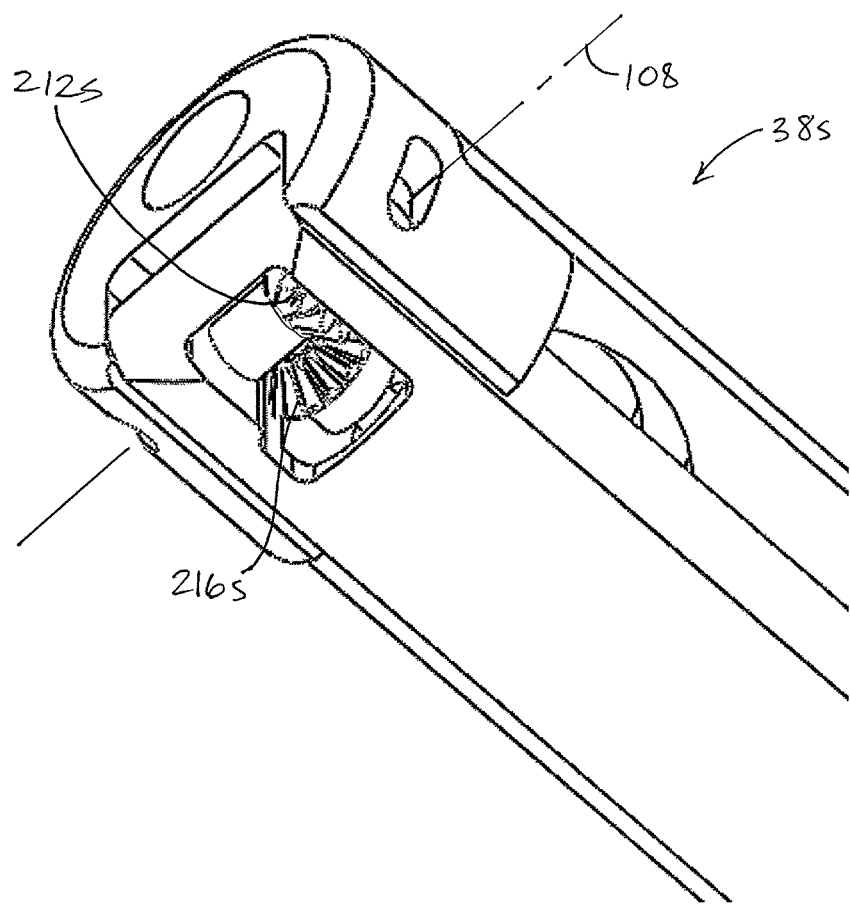

FIGS. 21A-21B depict various views of an arm 104*r* suitable for use with device 38*q*. Arm 104*r* is substantially similar to arm 104*q*, but first set of teeth 340*r* are configured as a separate piece that is coupled to arm 104*r* (e.g., by way of pins or other fasteners). In some embodiments first set of teeth 340*r* comprise a material that is different than that of the arm.

FIGS. 22A-22E depict various views of another embodiment 38*s* of the present medical devices, which can also be used as part of one of the present systems. Medical device 38*s* is similar in several respects to medical devices 38*a*, 38*b*, 38*c*, 38*d*, 38*e*, 38*f*, 38*g*, 38*h*, 38*i*, 38*j*, 38*k*, 38*l*, 38*m*, 38*n*, 38*o*, 38*p*, 38*q*, and 38*r*, so generally only the differences between them will be described here. In particular, arm 104*s* is pivotally coupled to platform 100*s* such that arm 104*s* is rotatable at least 90 degrees around rotational axis 108 between a collapsed position and an expanded position. In the embodiment shown, medical device 38s comprises a motor 344s coupled to (e.g., internal to) arm 104s; a first gear 212s coupled in fixed relation to platform 100s; and a second gear 216s coupled to motor 344s. In the embodiment shown, medical device 38s is configured such that: if motor 344s is actuated to rotate second gear 212s in a first rotational direction 224 when arm 104s is in the collapsed position, then arm 104s will rotate from the collapsed position toward the expanded position. In some embodiments, medical device 38s further comprises: a third gear (not shown) rotatably coupled to platform 100s such that the third gear is configured to rotate around rotational axis 108 (e.g., to help distribute the load between first gear 212s and second gear 216s).

Figure 23A:
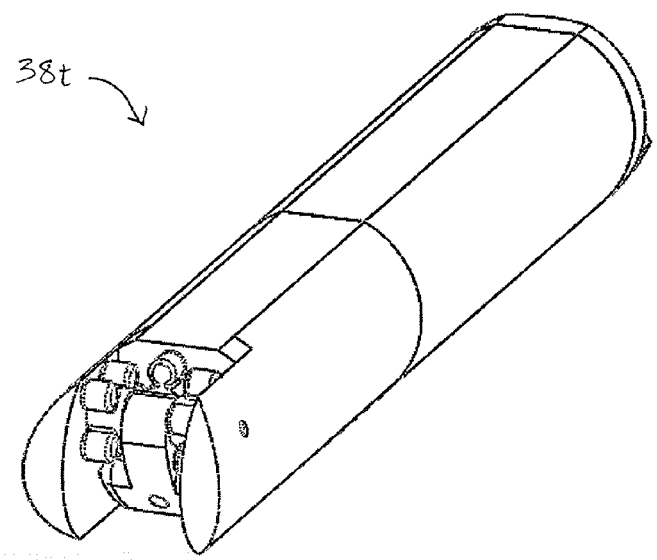
FIGS. 23A-23F depict various views of another embodiment of the present medical devices.
Figure 23B:
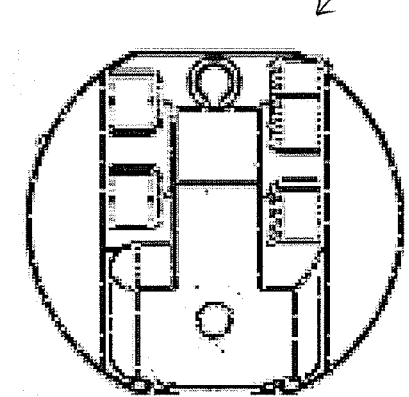
Figure 23C:
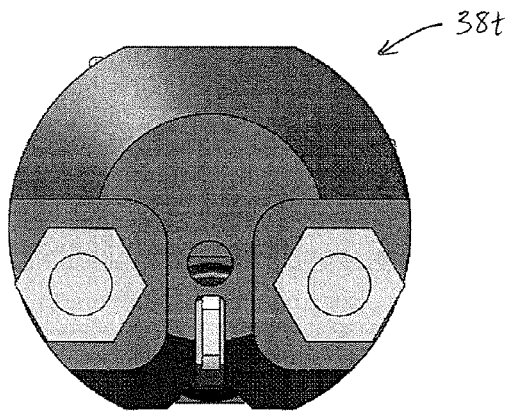
Figure 23D:
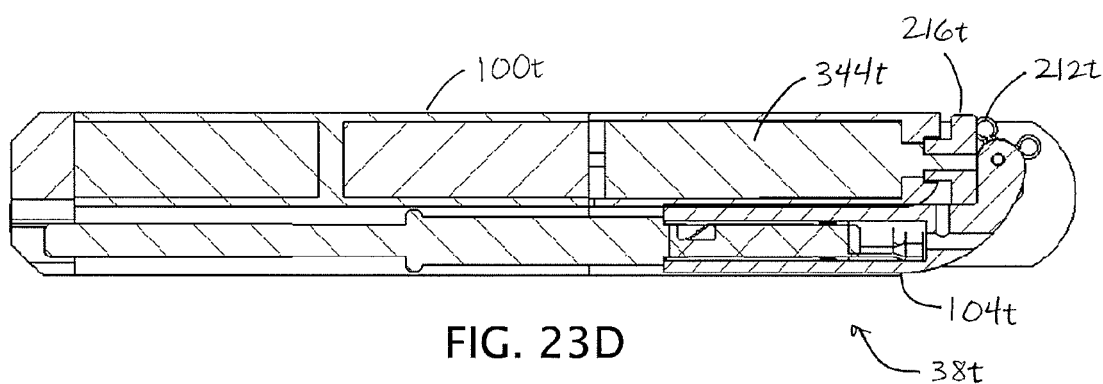
Figure 23E:
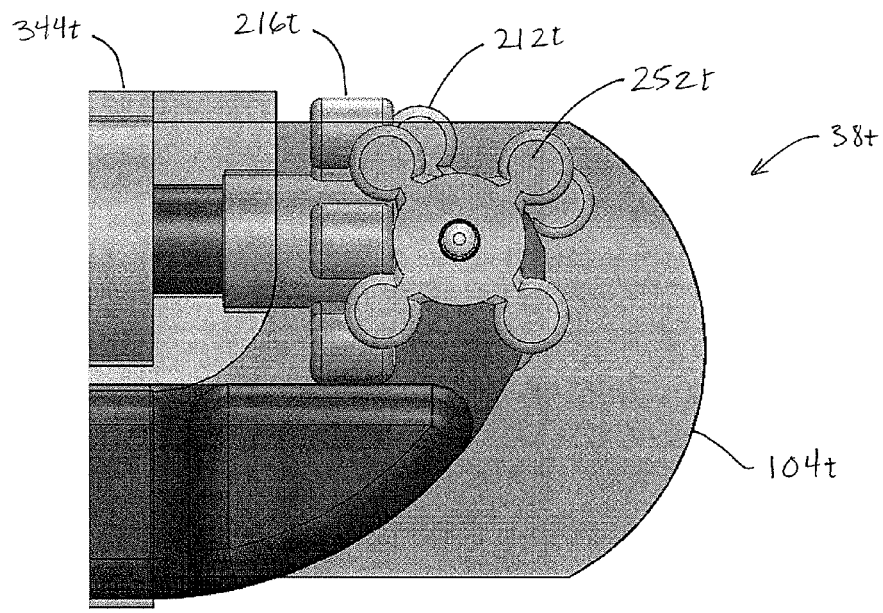
Figure 23F:
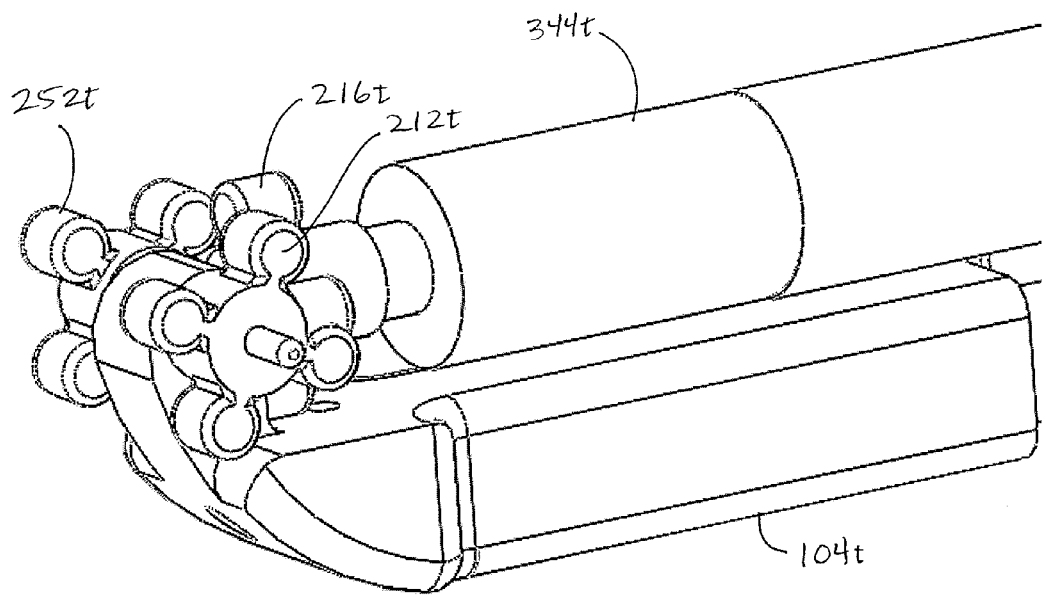

FIGS. 23A-23E depict various views of another embodiment 38t of the present medical devices, which can also be used as part of one of the present systems. Medical device 38t is similar in several respects to medical devices 38a, 38b, 38c, 38d, 38e, 38f, 38g, 38h, 38i, 38j, 38k, 38l, 38m, 38n, 38o, 38p, 38q, 38r, and 38s, so generally only the differences between them will be described here. In particular, medical device 38t comprises a motor 344t coupled to (e.g., internal to) platform 100t, a second gear 216t coupled to motor 344t, a first gear 212t coupled in fixed relation to arm 104t, and a third gear 252t rotatably coupled to arm 104t such that third gear 252t (e.g., to help distribute the load between first gear 212t and second gear 216t). As shown, each of first, second, and third gears 212t, 216t, 252t has a custom shape that is different from a standard toothed gear, and each gear instead comprises a plurality of substantially equally-sized, substantially circular protrusions from a central hub. FIG. 23F is a partially cutaway view that omits a portion of platform 100t to show portions of device 38t (including the gears) in more detail.

Figure 24A:
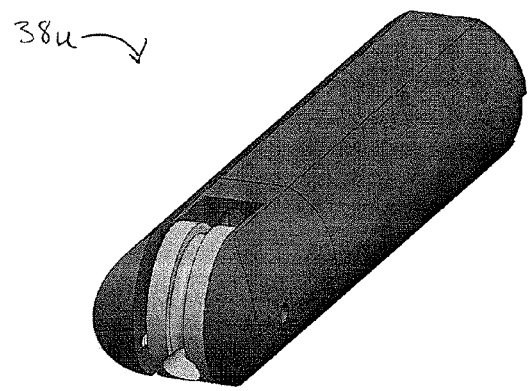
Figure 24B:
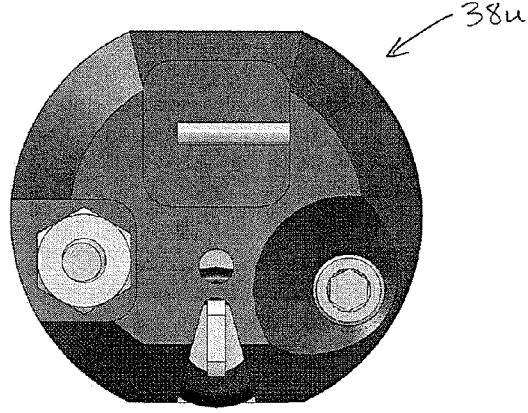
Figure 24C:
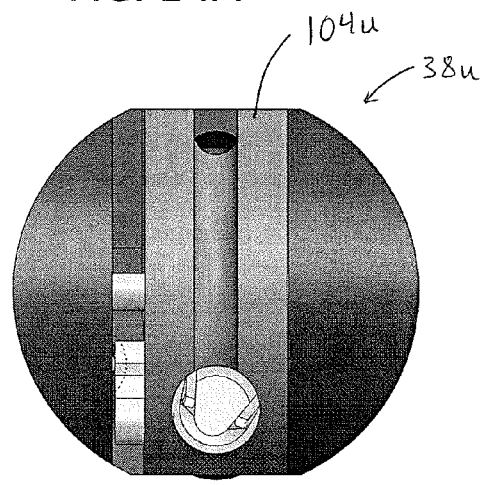
Figure 24D:
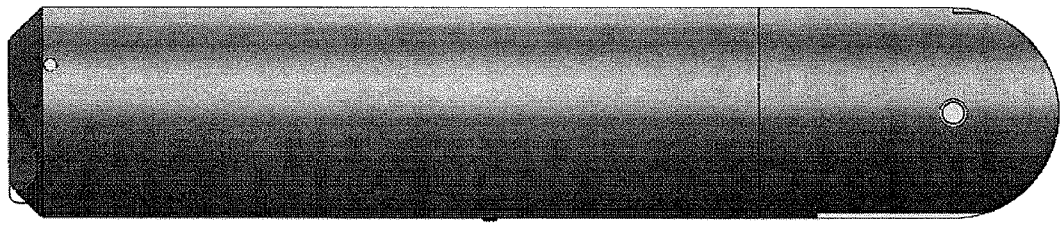

FIGS. 24A-24F depict various views of another embodiment 38u of the present medical devices, which can also be used as part of one of the present systems. Medical device 38u is similar in several respects to medical devices 38a, 38b, 38c, 38d, 38e, 38f, 38g, 38h, 38i, 38j, 38k, 38l, 38m, 38n, 38o, 38p, 38q, 38r, 38s, and 38t, so generally only the differences between them will be described here. In particular, medical device 38u is similar to device 38j, but comprises: a member 264u (e.g., non-threaded member 264u) movably (e.g., slidably) coupled to platform 100u; a shuttle 268u coupled to member 264u (e.g., via a pin or tab); and a shuttle arm 272u having a first end 276u coupled to shuttle 268u and a second end 280u coupled to hub 260u of arm 104u. In the embodiment shown, medical device 38u is configured such that: a tool (e.g., 220) can be coupled to member 264u to move (e.g., slide) member 264u (e.g., by pushing member 264u with the tool); and if member 264u is moved in a substantially linear first direction 284 when arm 104u is in the collapsed position (FIG. 24E), then shuttle 268u will travel in first direction 284 to cause arm 104u to rotate from the collapsed position (FIG. 24E) toward the expanded position (FIG. 24F). In the embodiment shown, medical device 38u further comprises: a spring 348 configured to bias member 268u in second direction 288 such that if arm 104u is deployed and member 268u is moved in second direction 288, spring 348 will cause arm 104u to rotate toward the collapsed position.

In any of the present embodiments, the medical device e.g., devices 38a, 38b, 38c, 38d, 38e, 38f, 38g, 38h, 38i, 38j, 38k, 38l, 38m, 38n, 38o, 38p, 38q, 38r, 38s, 38t, and 38u) can be sterilized. For example, embodiments of the present medical devices can comprise a sterilized and/or sterile platform (e.g., 100a, 100b, 100c, etc.) and/or a sterilized and/or sterile arm (e.g., 104a, 104b, 104c, etc.). Embodiments of the present medical devices (e.g., devices 38a, 38b, 38c, 38d, 38e, 38f, 38g, 38h, 38i, 38j, 38k, 38l, 38m, 38n, 38o, 38p, 38q, 38r, 38s, 38t, and 38u) can be made by any suitable method and can comprise any suitable material or materials. For example, the platforms (e.g., 100a, 100b, 100c, etc.) and arms (e.g., 104a, 104b, 104c, etc.) can be machined by conventional subtractive methods such as milling or turning, or can be formed by additive methods such as those used for rapid prototyping; and can comprise suitable biocompatible materials such as plastics, metals, composites, alloys, and the like. Various other components such as, for example, bearings, gears, fluid cylinders, cables, conductors, conduits, and the like can be obtained from common mechanical/electrical suppliers, such as, for example, Small Parts, Inc., Florida, USA; McMaster-Carr Supply Company, Georgia, USA; Stock Drive Products/Sterling Instrument, New York, USA; SMC Corporation of America, Indiana, USA; Bimba Manufacturing Company, Illinois, USA; Festo Corporation, New York, USA; Faulhaber Group, Germany; and MicroMo Electronics, Inc., Florida, USA. Similarly, the parts or components of embodiments of the present systems and/or medical devices can be assembled through any suitable means including, for example, conventional manual techniques, fastening, press-fitting, securing with biocompatible epoxies or adhesives, and the like. In embodiments of the present systems and medical devices that include tether 42, and tether 42 serves to couple the tool of the device to a power source, the source can be a hydraulic source such as a fluid (liquid or gas) pressure source. Examples of fluid pressure sources include hand pumps, electric pumps, compressed gas bottles with a pressure regulator, or the like. In embodiments in which the power source that tether 42 can couple to the tool is an electrical power source, examples of such power sources include batteries, electric amplifiers, and the like. Other examples of electrical power sources that can be used where the tool is a cautery tool include, as mentioned above, electrosurgery units, such as, for example, an electrosurgery unit or power source available from suppliers such as, for example, ValleyLab, Colorado, USA; Erbe USA, Inc., Georgia, USA. In some embodiments, tether 42 can include more than one conductors and/or conduits. For example, tether 42 can include one conductor and one conduit, two conductors and one conduit, three conductors, or the like, as appropriate for delivering hydraulic fluid (gas or liquid) and/or electric power to various components of the relevant device (e.g., devices 38a, 38b, 38c, 38d, 38e, 38f, 38g, 38h, 38i, 38j, 38k, 38l, 38m, 38n, 38o, 38p, 38q, 38r, 38s, 38t, and 38u). By of way additional examples, the tether 42 can include a conductive portion coaxially around a fluid conduit, or can include a conductive portion (insulated) within a fluid conduit (e.g., configured to permit fluid to flow within the conduit adjacent to the conductor).

The various embodiments of the present systems, apparatuses, devices, and methods described in this disclosure can be employed and/or applied for any suitable medical or surgical procedures, including, for example, natural orifice transluminal endoscopic surgery (NOTES), single-incision laparosopic surgery (SILS), single-port laparoscopy (SLP), and others.

The various illustrative embodiments of systems, apparatuses, devices, and methods described herein are not intended to be limited to the particular forms disclosed. Rather, they include all modifications and alternatives falling within the scope of the claims. For example, although the version of cam slots 304k shown in platform 100k of device 38k extend through the platform in which they reside such that slots 304k, in other embodiments, slots 304l may extend only partially into the respective portions of the platform in which they reside such that slots 304*l* are not visible from either side of the platform (e.g., as in device 38*l* of FIGS. 15A-15C).

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A medical device comprising:
   a platform;
   an arm having a hub that is pivotally coupled to the platform such that the arm is rotatable at least 90 degrees around a rotational axis between a collapsed position and an expanded position;
   a threaded member rotatably coupled to the platform;
   a shuttle coupled to the threaded member; and
   a shuttle arm having a first end coupled to the shuttle and a second end coupled to the hub of the arm;
   where the medical device is configured such that:
      a tool can be coupled to the threaded member such that the tool can be rotated to rotate the threaded member; and
      if the threaded member is rotated in a first rotational direction when the arm is in the collapsed position, then the shuttle will travel in a substantially linear first direction to cause the arm to rotate from the collapsed position toward the expanded position.

2. The medical device of claim 1, where the medical device is configured such that:
   if the threaded member is rotated in a second rotational direction when the arm is in the expanded position, then the shuttle will travel in a substantially linear second direction substantially opposite the first direction to cause the arm to rotate from the expanded position toward the collapsed position.

3. The medical device of claim 1, where the threaded member is configured to rotate around a member axis.

4. The medical device of claim 3, where the arm is rotatable in a rotational plane, and the member axis is substantially parallel to the rotational plane.

5. The medical device of claim 1, where the platform comprises at least one of a magnetically-attractive material and a material capable of being magnetically-charged.

6. The medical device of claim 2, where the threaded member is configured to rotate around a member axis.

7. The medical device of claim 2, where the platform comprises at least one of a magnetically-attractive material and a material capable of being magnetically-charged.

8. The medical device of claim 3, where the platform comprises at least one of a magnetically-attractive material and a material capable of being magnetically-charged.

9. The medical device of claim 4, where the platform comprises at least one of a magnetically-attractive material and a material capable of being magnetically-charged.

* * * * *